United States Patent [19]

Boyd et al.

[11] Patent Number: 5,665,603
[45] Date of Patent: Sep. 9, 1997

[54] THIOHYDANTOIN FORMATION AND SELECTIVE MODIFICATION OF THE CARBOXY TERMINUS OF AN ASPARTIC ACID- AND/OR GLUTAMIC ACID-CONTAINING PROTEIN

[75] Inventors: Victoria L. Boyd, San Carlos; MeriLisa Bozzini, Burlingame; Robert J. DeFranco, San Carlos, all of Calif.

[73] Assignee: The Perkin-Elmer Corporation, Foster City, Calif.

[21] Appl. No.: 272,496

[22] Filed: Jul. 8, 1994

Related U.S. Application Data

[63] Continuation-in-part of Ser. No. 96,658, Jul. 26, 1993.
[51] Int. Cl.$^6$ .................................................. A61K 38/02
[52] U.S. Cl. .............................. 436/90; 436/89; 530/340; 530/345
[58] Field of Search ............................ 530/340, 345; 436/89, 90

[56] References Cited

U.S. PATENT DOCUMENTS

| | | | |
|---|---|---|---|
| 4,935,494 | 6/1990 | Miller | 530/345 |
| 5,041,388 | 8/1991 | Boyd et al. | 436/89 |
| 5,049,507 | 9/1991 | Hawke et al. | 436/89 |
| 5,051,368 | 9/1991 | Boyd et al. | 436/89 |
| 5,066,785 | 11/1991 | Miller | 530/345 |
| 5,185,266 | 2/1993 | Boyd et al. | 436/89 |
| 5,304,497 | 4/1994 | Boyd et al. | 436/89 |

FOREIGN PATENT DOCUMENTS

| | | |
|---|---|---|
| WO90/05739 | 5/1990 | WIPO . |
| WO91/09868 | 7/1991 | WIPO . |

OTHER PUBLICATIONS

Stark, "Sequential degradation of peptides from their carboxyl termini with ammonium thiocyanate and acetic anhydride," Biochemistry, 7: 1796–1807 (1968).

Cromwell et al, "Determination of the carboxyl termini of proteins with ammonium thiocyanate and acetic anhydride, wtih direct identification of the thiohydantoin," Biochemistry, 8: 4735–4740 (1969).

Cosmatos et al., "Peptidsynthesen uber N–phosphorylaminosaure-phosphorsaureanhydride," Peptidsynthesen, Jahrg. 94, pp. 2644–2655 (1961).

Laursen et al., "Solid–phase methods in protein sequence analysis," Methods of Biochemical Analysis, 26: 201–272 (1980).

Meuth et al., "Stepwise sequence determination from thecarboxyl terminus of peptides," Biochemistry, 21: 3750–3757 (1982).

Kenner et al., "Selective removal of the C–terminal residue as a thiohydantoin. The use of diphenyl phosphorisocyanatidate," Peptides. Part IV. pp. 673–678 (1953).

Boyd et al., "Sequencing of peptides and proteins from the carboxy terminus," Anal. Biochemistry, 206: 344–352 (1992).

*Primary Examiner*—David Lukton
*Attorney, Agent, or Firm*—Vincent M. Powers

[57] ABSTRACT

A method of forming a thiohydantoin from an N-protected amino acid is described. The method employs a phosphate compound selected from the group consisting of

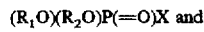

and

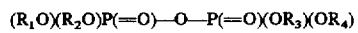

to form acylphosphate moieties from the carboxyl groups of internal aspartic acid and glutamic acid residues and an acylphosphate moiety at a C-terminal carboxyl. The later acylphosphate, unlike the internal acylphosphates, spontaneously cyclizes to an oxazolone, which is less reactive with nucleophilic reagents. $R_1$ and $R_2$ are each alkyl, aryl, or alkaryl groups which are the same or different and which may be covalently linked to each other; $R_3$ and $R_4$ are each alkyl, aryl, or alkaryl groups which are the same or different and which may be covalently linked to each other; and X is a leaving group, such as chlorine or bromine, which is substantially unreactive towards thiohydantoins. The acylphosphate and oxazolone moieties are then reacted with a thiocyanate reagent under conditions effective to convert the internal acylphosphates to amides and the terminal oxazolone to thiohydantoin, thereby permitting selective C-terminal thiodantionation of aspartic acid- and/or glutamic acid-containing proteins.

24 Claims, 15 Drawing Sheets

1) Tetraphenylpyrophosphate
   or
   Chlorophosphate
2) TMS-ITC

XR₂
BASE

Substantially
anhydrous TMS-ITC
or NH₄SCN

Fig. 5D
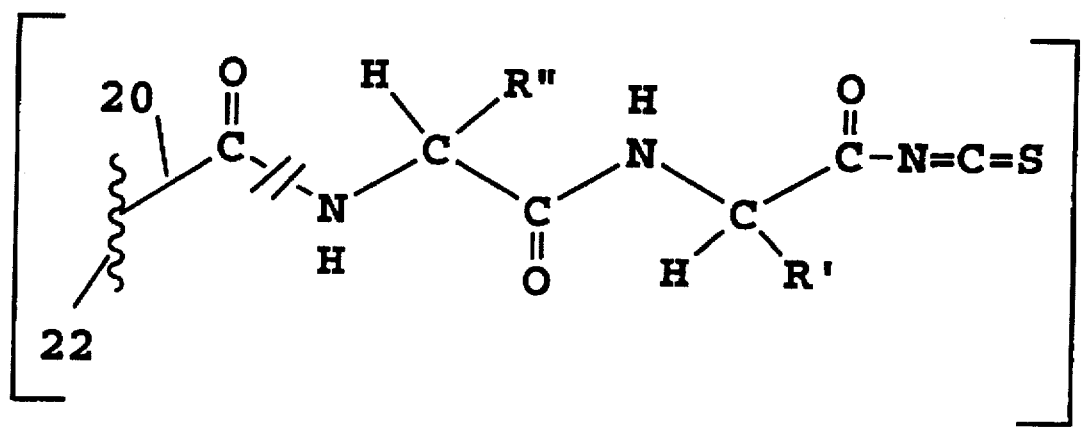
+
Cleaved, modified thiohydantoin derivative
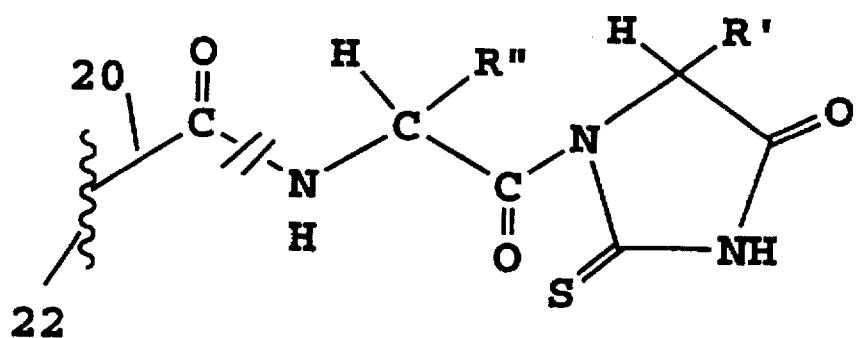
Fig. 5E

THIOHYDANTOIN FORMATION AND SELECTIVE MODIFICATION OF THE CARBOXY TERMINUS OF AN ASPARTIC ACID- AND/OR GLUTAMIC ACID-CONTAINING PROTEIN

This is a continuation-in-part of co-pending application Ser. No. 08/096,658 filed 26 Jul. 1993, which is incorporated herein by reference.

FIELD OF THE INVENTION

The present invention relates to a method of synthesizing amino acid thiohydantoins and for selectively modifying the carboxy terminus of an aspartic acid- and/or glutamic acid-containing protein, particularly in C-terminal protein sequencing.

REFERENCES

Bailey, J. M., et al., U.S. Pat. No. 5,180,807.
Boyd et al., U.S. Pat. No. 5,185,266.
Boyd et al., U.S. Pat. No. 5,051,368.
Hawke, U.S. Pat. No. 4,837,165.
Hawke et al., U.S. Pat. No. 5,049,507.
Hawke, D. H. et al., *Anal Biochem*, 166:298 (1987). Inglis, A. S., et al., in *Methods in Protein Sequence Analysis* (Wittmann-Liebold, B., ed.) Springer Verlag, 137–144 (1988).
Johnson, T. B., et al., *J. Am. Chem. Soc.*, 48:103 (1911).
Kenner et at., J. Chem. Soc. (1953), 673–678.
Miller, U.S. Pat. No. 4,935,494.
Miller, C. G., et al., in *Methods in Protein Sequence Analysis* (Wittmann-Liebold, B., ed.) Springer Verlag, 145–151 (1988).
Schlack, P., and Kumpf, W. (1926) *Hoppe-Seyler Z. Physiol. Chem.* 154:125.
Stark, G. R., *Biochemistry*, 7(5);1796–1807 (1968).

BACKGROUND OF THE INVENTION

A variety of chemical methods for converting N-protected amino acids, including the C-terminal amino acid residues of peptides, to a corresponding thiohydantoin (TH) have been proposed. TH formation is useful, for example, in C-terminal amino acid sequencing, where a C-terminal amino acid of a peptide is sequentially (a) converted to its corresponding TH, (b) cleaved from the remaining peptide, and (c) identified in term of the attached amino acid, e.g., by HPLC. Another use of such reaction methods is in preparing amino acid TH compounds for use as standards, e.g., in C-terminal sequencing.

The conversion of N-protected amino acids to corresponding amino acid TH's was first proposed in 1911 by Johnson et al. (1911) and in 1926 by Schlack and Kumpf (Schlack et al., 1926). A number of improvements to this early method have since been proposed (see, e.g., Stark, 1968; Boyd et al., U.S. Pat. No. 5,051,368; Hawke, 1987; Hawke, U.S. Pat. No. 4,837,165; Hawke et al., U.S. Pat. No. 5,049,507; Inglis; Miller, 1988; and Miller, U.S. Pat. No. 4,935,494).

Stark's method for making 2-thiohydantoins, employing acetic anhydride as activating agent, often results in low yields and in complicating side reactions. Similarly, the method of Hawke et al. (U.S. Pat. No. 5,049,507), which employs an acyl-isothiocyanate moiety for generating the thiohydantoin, suffers from many side reactions.

Recent efforts to improve thiohydantoin-based methods have focused on improving the efficiency of forming the C-terminal activated ester. For example, Boyd et al. (U.S. Pat. No. 5,051,368) have proposed a method of forming a C-terminal thiohydantoin that employs N-substituted ketenimines, generated by Woodward's Reagent K, to form the activated ester. However Reagent K is not soluble in organic solvents, and the reaction of the ketenimine intermediate (which is unstable in solution) with the polypeptidyl C-terminal carboxylate must usually be carried out slowly at room temperature.

Kenner et at. (1953), and more recently, Bailey et al. (U.S. Pat. No. 5,180,807) have used phosphoroisothiocyanatidate for preparing C-terminal thiohydantoins. Although the reagent used in the method performs the dual roles of carboxyl activation and thiodantoin formation, the reagent is inherently unstable and results in low TH yields.

A further problem in forming C-terminal thiohydantoins concerns the reactivity of the non-terminal carboxy groups appearing on the side-chains of aspartic and glutamic acid. Typically, these internal carboxy groups are derivatized along with the C-terminal carboxy. If these modified residues later appear as the C-terminal residue in the sequencing process, they frequently interfere with sequencing by giving rise to alternative side products during thiodantoin formation, or they are difficult or impossible to distinguish from other residues after cleavage.

SUMMARY OF THE INVENTION

The present invention includes a method of selectively converting a C-terminal N-protected amino acid to a corresponding amino acid thiohydantoin. An important feature of the invention is generating an oxazolone moiety at a C-terminal carboxyl and acylphosphate moieties at side-chain carboxyls of a protein or peptide sample. Preferably, this is accomplished by reacting the protein or peptide sample with a carboxyl-activating compound selected from the group described below to form acylphosphate moieties at both the terminal and side-chain carboxyls. The terminal acylphosphate then cyclizes to form an oxazolone moiety which is less reactive to nucleophilic reagents that can be employed to selectively convert the side-chain acylphosphates to amides.

Preferably, the carboxyl-activating compounds of the invention are selected from the group consisting of:

to form a carboxyl-activated N-protected amino acid (referred to herein as an "acylphosphate"), where $R_1$ and $R_2$ are each alkyl, aryl, or alkaryl groups which are the same or different and which may be covalently linked to each other; $R_3$ and R4 are each alkyl, aryl, or alkaryl groups which are the same or different and which may be covalently linked to each other; X is a leaving group which is substantially unreactive towards thiohydantoins; and Y is oxygen, sulfur, or disulfide. In one preferred embodiment, X is bromine or chlorine and Y is oxygen. The activated amino acid is then reacted with a thiocyanate reagent under conditions effective to convert the carboxyl-activated N-protected amino acid, i.e. the acylphosphate, to an N-protected amino acid thiohydantoin.

In one embodiment, the method is employed to identify the C-terminal amino acid residue of a peptide or protein sample that has aspartic acid and/or glutamic acid residue, particularly in its C-terminal region. In this case, the N-protected amino acid is the C-terminal amino acid of a peptide. In accordance with the method of the invention, a start-up sequencing cycle forms acylphosphate moieties on both carboxyls of aspartic acid and glutamic acid residues and the carboxyl at the C-terminus. The later acylphosphate immediately cyclizes to form an oxazolone, whereupon the sample is treated with a nucleophilic reagent, preferably an amine nucleophile, to amidate the acylphosphate moieties of the internal aspartic acid and glutamic acid residues, while the terminal oxazolone remains substantially unaffected.

In another embodiment, the method is used in C-terminal sequencing wherein a plurality of C-terminal residues in a polypeptide are sequenced. In a preferred method, following formation of a first peptidyl thiohydantoin as outlined above, the thiohydantoin is reacted with an alkylating agent of the type disclosed in U.S. Pat. No. 5,185,266, to promote cleavage of the thiohydantoin from the next-in C-terminal residue.

For C-terminal sequence analysis of a peptide, the invention includes a sequencing method comprising pretreatment of the peptide with phenylisocyanate to block the $\epsilon$-amino groups of lysine residues and to promote dehydration of serine and threonine residues.

In another embodiment, for improved identification of aspartate and glutamate residues and reduction of internal cleavage at aspartate residues, the method includes formation of a peptidyl thiohydantoin by the procedures outlined above, followed by reaction of the resultant peptidyl thiohydantoin with a selected alcohol to esterify carboxylate side chains in the peptide.

In another embodiment, the carboxy groups in the side-chains of internal aspartic acid and glutamic acid residues are converted to amides by reacting the acylphosphate intermediates with an appropriate nucleophilic reagent, such as ammonia, piperidine, or the like. Preferably, the nucleophilic reagent is provided as a conjugate salt of the thiocyanate ion and is selected so that the modified aspartic acid and glutamic acid residues can be distinguished from the other amino acids after thiohydantoination and cleavage.

Preferably, the acylphosphate intermediates are formed by reacting a protein or peptide sample with a pyrophosphate compound defined by the formula:

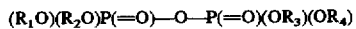

where $R_1$, $R_2$, $R_3$, and $R_4$ are defined as described above. Pyrophosphates of the above type are less reactive towards the oxazolone moiety than the di-substituted phosphate compounds of the invention, thereby reducing the yield of undesired side products.

In another embodiment, the method is used in the preparation of amino acid thiohydantoin standards, e.g., for use in C-terminal sequence analysis by HPLC.

These and other objects and features of the invention will become more fully apparent when the following detailed description of the invention is read in conjunction with the accompanying drawings.

BRIEF DESCRIPTION OF THE FIGURES

FIGS. 5A–5E illustrate an application of the method of the invention to C-terminal peptide-sequencing;

DETAILED DESCRIPTION OF THE INVENTION

I. Definitions

The following terms, as used herein, have the meanings as indicated: Preferably, the term "acylphosphate" means a radical defined by the formula:

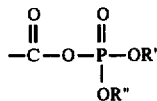

wherein R' and R" are typically defined as $R_1$ and $R_2$ above.

Preferably, the term "oxazolone" usually means a radical defined by the formula:

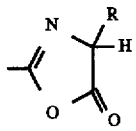

wherein R is typically an amino acid side-chain.

Figure 1A:
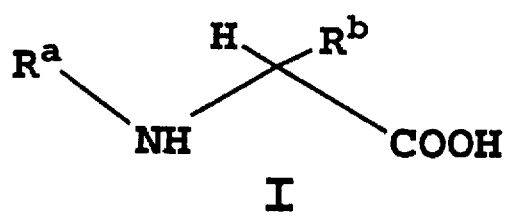
FIGS. 1A–1C show the structures of an N-protected amino acid (FIG. 1A), an N-protected amino acid thiohydantoin (FIG. 1B), and a deprotected amino acid thiohydantoin (FIG. 1C), as defined herein.

"N-protected amino acid" refers to an amino acid or a polypeptide having a protecting group bonded to its $\alpha$-amino group. Typical protecting groups include Fmoc, Boc, acyl, polypeptidyl, and amine-reactive groups bound to a solid support, as well-known in the art. A structural formula for an N-protected amino acid is shown in FIG. 1A, where $R^a$ represents the protecting group. The amino acid, whose side chain is represented by $R^b$, may have additional protecting groups to mask an amine, carboxylate, sulfhydryl, or hydroxyl group in the side chain.

"Peptide" and "polypeptide" refer to a peptide containing two or more amino acid residues, including a native or denatured protein. In FIG. 1A, the protected amino acid is the C-terminal residue of a peptide if the protecting group ($R^a$) includes one or more amino acid residues coupled to the C-terminal residue via an amide bond.

Figure 1B:
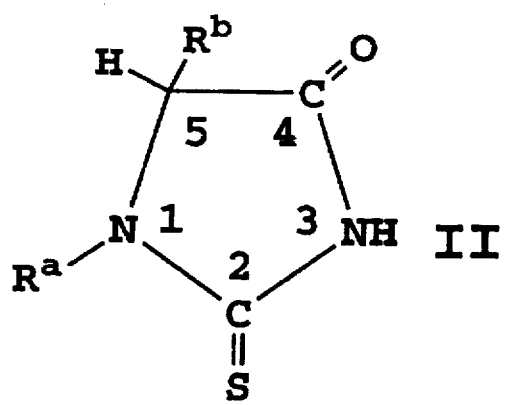
Figure 1C:
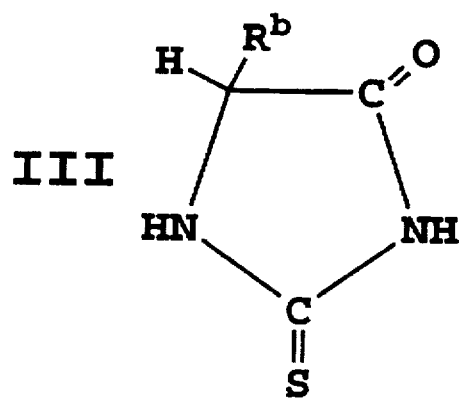

"Amino acid thiohydantoin" or "amino acid TH" refers to members of the class of compounds having the structural formula shown in FIG. 1B, where $R^b$ is an associated side chain of an amino acid, and the numerals 1 to 5 indicate the conventional numbering scheme for the thiohydantoin. In accordance with the present invention, a thiohydantoin is formed from an N-protected amino acid, which may include an N-protected free amino acid or the C-terminal amino acid of a peptide. As used herein, an amino acid TH can have an N-protecting group, as shown at II in FIG. 1B, or can be deprotected, i.e., released from or lacking an N-protecting group, as shown in FIG. 1C.

"N-protected peptidyl thiohydantoin" and "C-terminal peptidyl thiohydantoin" refer to an N-protected thiohydantoin in which the protecting group is a polypeptide.

"Isothiocyanate reagent" or "thiocyanate reagent" refers to a chemical species that can provide a thiocyanate [SCN]$^-$ anion.

"Solid support" or "solid phase support" refers to any solid support that has surface functionality or can be derivatized to have surface functionality. Preferably, the surface functionality can interact with an amino group of a peptide so as to bind the peptide to the support. Such binding can be by covalent linkage, ionic interactions, and/or hydrophobic interactions. Exemplary solid supports include, but are not limited to, Sepharose™, an aminopropyl derivative of silica, aminopropyl-CPG (controlled pore glass), aminoethyl cellulose, Tris-aryl$^R$-NH, glass beads, polyacrylamide particles, 1,4-phenylene diisothiocyanate (DITC) glass, functionalized polystyrene, polyethylene, membrane supports such as functionalized PVDF, and the like.

"In the C-terminal region of a thiohydantoin" refers to a residue which is located in a polypeptide near the C-terminus of the polypeptide (within 50 residues of the C-terminal residue).

II. Formation of N-Protected Amino Acid Thiohydantoin

In accordance with the invention, a N-protected amino acid, preferably at the C-terminus of a protein or peptide, is reacted with a phosphate compound selected from the group consisting of

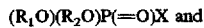

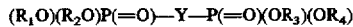

to form an activated N-protected amino acid containing a acylphosphate which forms a 2-alkyl-5(4H)-oxazolone through intramolecular cyclization. The oxazolone is then reacted with a thiocyanate to form the corresponding N-protected amino acid thiohydantoin. Preferably, acylphosphate moieties generated from carboxyls on the side-chains of internal aspartic acid and glutamic acid residues are converted to amides by reaction with an appropriate nucleophilic reagent while the C-terminus remains oxazolone. Preferably, the nucleophilic reagent includes an amine nucleophile.

Figure 2A:
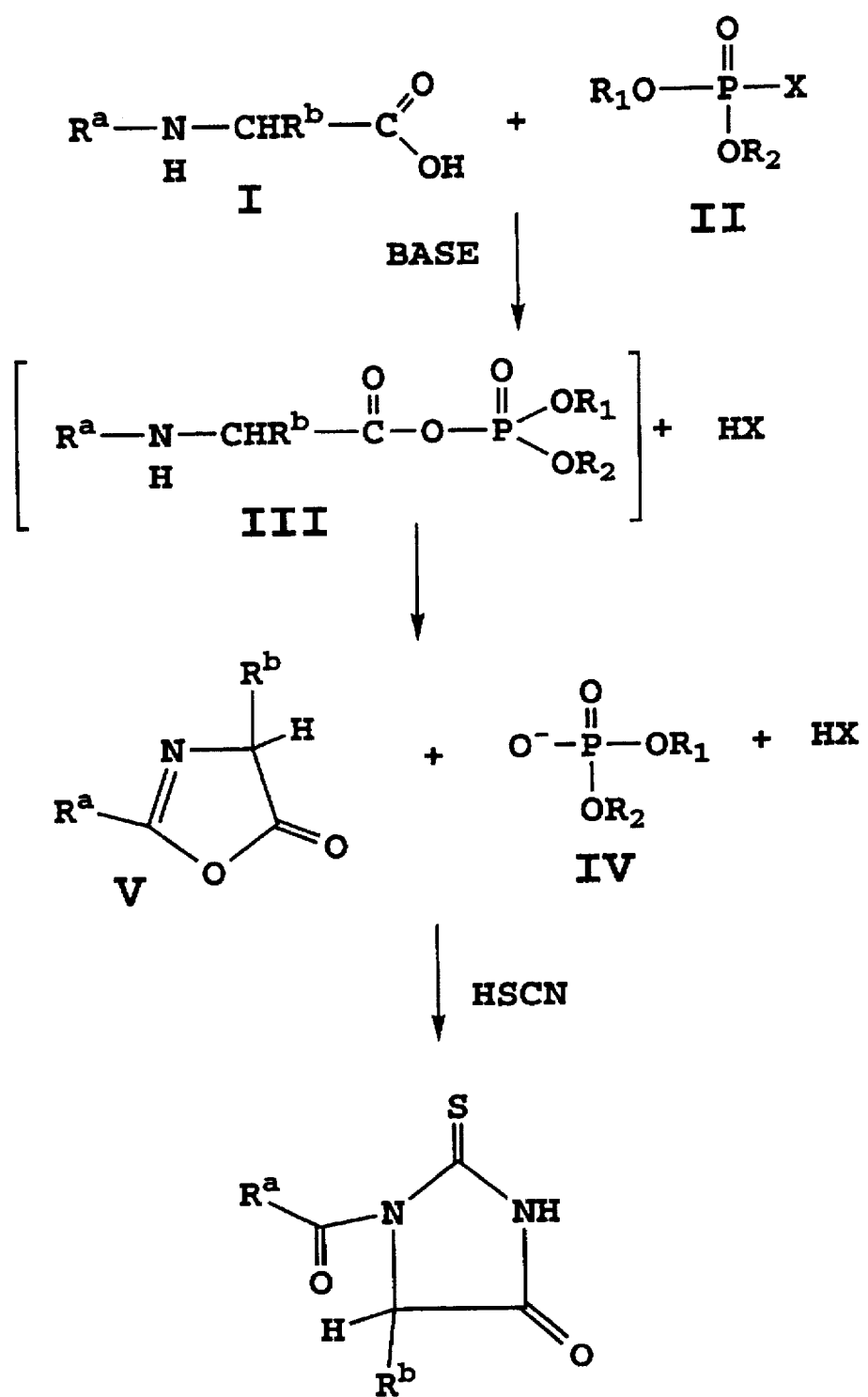
FIG. 2A and 2B show a general reaction scheme for forming an N-protected amino acid thiohydantoin from acylphosphate and oxazolone intermediates according to the present invention.
Figure 2B:
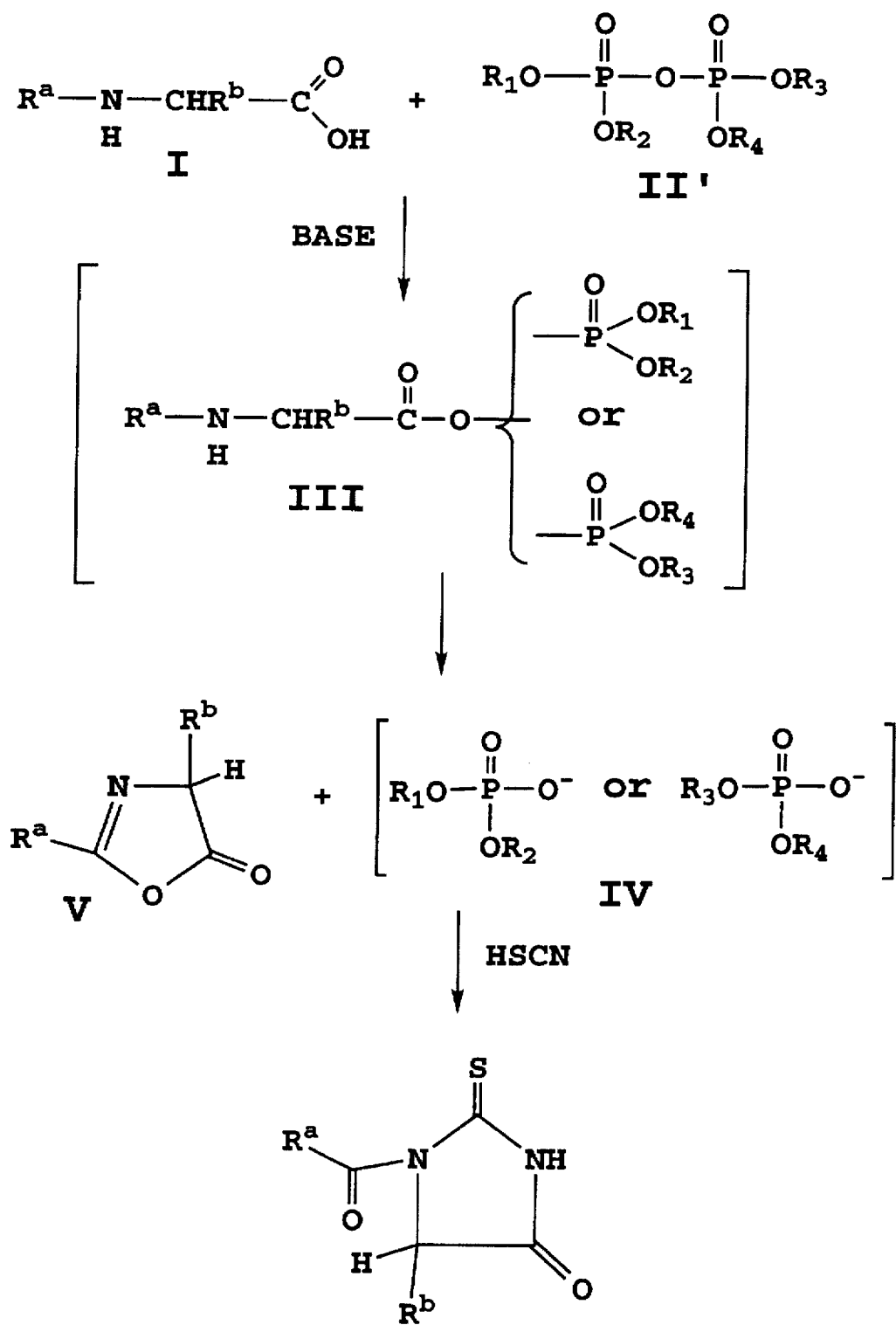

A reaction scheme for preparing an N-protected thiohydantoin is illustrated in FIGS. 2A and 2B. Reaction of the C-terminal carboxylic acid group of N-protected amino acid 1 with reactive phosphate compound 2, or 2' in FIG. 2B, in the presence of a suitable base, yields mixed anhydride 3, which in the case of a C-terminal carboxyl immediately cyclizes to an oxazolone 5 with a release of phosphate 4. Treatment of oxazolone 4 with a thiocyanate leads to the indicated thiohydantoin.

Carboxyl-activating compounds of the invention include phosphate and pyrophosphate compounds selected from the group consisting of

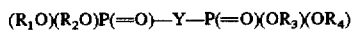

where $R_1$ and $R_2$ are each alkyl, aryl, or alkaryl groups which are the same or different and which may be covalently linked to each other; and $R_3$ and $R_4$ are each alkyl, aryl, or alkaryl groups which are the same or different and which may be covalently linked to each other. The alkyl groups may be linear or branched and may include 1 to 10 carbon atoms, but preferably including from 1 to 6 carbon atoms. The aryl groups include phenyl, pyridyl, naphthyl, furyl, and the like, which may contain non-hydrogen substituents at one or more ring positions. Alkaryl groups include benzyl, phenethyl, and the like, where the alkaryl group contains an aryl group which is linked to a phosphorus-linked oxygen atom by one or more methylene groups. $R_1$ and $R_2$ or $R_3$ and $R_4$ may be linked, as in a phenylene or cycloalkylene ring, for example. In general, $R_1$ through $R_4$ are selected for compatibility with the reaction solvent, solubility, and for inertness towards the reactants, intermediates, such as oxazolone, and thiohydantoin products that are employed or generated in the method.

Leaving group X is selected for facile displacement by the C-terminal carboxylate group of the N-protected amino acid, while being substantially inactive as a nucleophile towards displacement of the phosphate moiety in acylphosphate product V. It is also desirable for X to be substantially inert towards reaction with thiohydantoins. Suitable leaving groups include halogens, i.e., chloride, bromide, iodide, or fluoride; and sulfonate groups, such as tosylate (p-toluene sulfonate), triflate (trifluoromethane sulfonate), or sulfonate itself. Preferably, X is chloride or bromide.

Preferably, Y is oxygen, sulfur, or disulfide. More preferably, Y is oxygen.

Exemplary phosphate compounds for use in the invention include diphenyl phosphochloridate, 1,2-phenylene phosphorochloridate, 2-chloro-1,3,2-dioxophospholane-2-oxide, bis-(2,2,2-trichloroethyl) phosphorochloridate, and 1,2-phenylene phosphorochloridate, all of which are available from commercial sources (e.g., Aldrich Chemical Co., Milwaukee, Wis.).

Preferably, in the pyrophosphate carboxyl-activating compounds of the invention $R_1=R_2=R_3=R_4=$ ethyl or phenyl. Synthesis of pyrophosphate carboxyl-activating compounds is described in Corby et at, J. Chem. Soc., p. 1234 (1952), and/or Stec et al, U.S. Pat. No. 5,151,510.

The reaction between 1 and 2 (FIG. 2A) or 2' (FIG. 2B) to form acylphosphate 3 is carried out in the presence of a base to promote deprotonation of the C-terminal carboxylic acid in 1, and to neutralize the HX species formed in the reaction (FIG. 2A). Suitable bases include tertiary mines, such as triethylamine (TEA), diisopropylethylamine (DIEA), and pyridines, e.g., 2,6-dimethylpyridine. More generally, the base is one which is substantially non-nucleophilic towards the acylphosphate 3 and thiohydantoin formed in the FIG. 2A and 2B reaction schemes.

In preparing acylphosphate 3 as outlined above, reactive phosphate compound 2 or 2' is present in an equimolar or excess amount (e.g., 1:1 to 10:1) with respect to the C-terminal carboxylate of the N-protected amino acid, and the concentration of base is preferably about equimolar with respect to reactive phosphate compound 2 or 2'. For microsequencing applications which involve sequencing of very small amounts of polypeptide, however, the reactive phosphate compound and base are used in much greater excess with respect to the C-terminal carboxylate to minimize reaction times and improve reaction yield.

The solvent used in the activation reaction is preferably an organic or polar aprotic solvent. Suitable solvents include acetonitrile, dimethylformamide (DMF), methylene chloride, and ethereal solvents, for example.

Typically, reaction of reactive phosphate compound 2 or 2' with N-protected amino acid 1 is complete within 1–30 minutes, usually in 5 to 10 minutes, at a temperature of 20°–55° C. By contrast, TH formation by activation with acetic anhydride (Stark, 1968) typically requires at least 30 minutes at high temperature (60°–80° C.). Activation with Woodward Reagent K, which must be carried out near room temperature, typically requires several hours.

With continued reference to FIGS. 2A and 2B, di-substituted phosphate 4 is eliminated from acylphosphate 3 during an intramolecular cyclization with formation of a 2-alkyl-5(4H)-oxazolone 5 Oxazolone 5 is then reacted with a thiocyanate to form an N-protected amino acid thiohydantoin.

Figure 3:
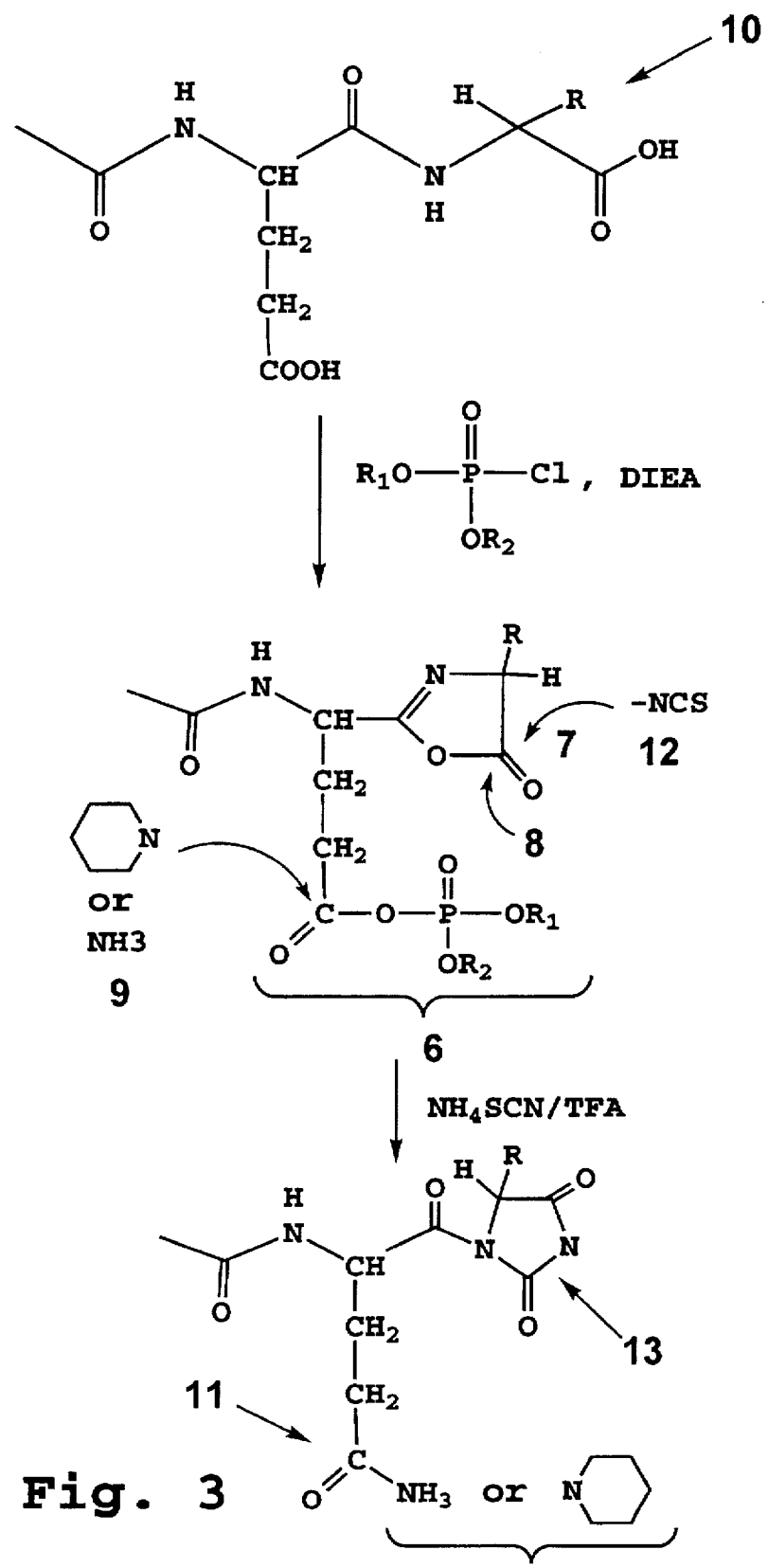
FIG. 3 shows a general reaction scheme for the formation of acylphosphates at side-chain and terminal carboxyls in accordance with the present invention.

As shown in FIG. 3, in a protein or peptide sample 10 having a penultimate glutamic acid, an acylphosphate 6 is formed on the side-chain carboxy of the glutamic acid, while an oxazolone moiety 7 is formed at the C-terminus by reaction with a phosphate compound of the invention in the presence of a base, such as DIEA. Since the carbonyl carbon 8 of the oxazolone is less reactive towards nucleophilic reagents, e.g. amines, than that of a acylphosphate, the side-chain acylphosphate 6 (which does not undergo intramolecular cyclization to an oxazolone) can be selectively modified by treatment with a nucleophilic reagent, such as ammonia 9, piperidine, or the like, to form amide 11 while conditions are still basic. Later, when conditions are acidic, oxazolone moiety 7 reacts with thiocyanate 12 to form thiodantoin 13. Preferably, the nucleophilic reagent is delivered as a conjugate pair of the thiocyanate ion, such as in the form of ammonium thiocyanate, piperidine thiocyanate, or the like.

Thiocyanate reagents for use in the invention include ammonium thiocyanate, alkylammonium thiocyanates, metallothiocyanates (e.g., NaSCN, KSCN, AgSCH, and the like) silylisothiocyanates (e.g., trimethylsilylisothiocyanate), and pyridinium thiocyanates. Where the reagent is a metallothiocyanate, the reaction conditions preferably include a crown ether for promoting dissociation of the metal ion from the thiocyanate anion. Preferably, the thiocyanate reagent is ammonium thiocyanate whenever the protein or peptide sample does not contain internal aspartic acid and/or glutamic acid residues. Preferably, the thiocyanate reagent is piperidine thiocyanate when internal aspartic acid and/or glutamic acid residues are present in the protein or peptide sample. In both of these preferred embodiments, the amine component of the thiocyanate reagent serves as the nucleophilic reagent from amidating the internal carboxyl groups. Accordingly, an important feature of the embodiments is selecting appropriate pH to maximize amidation of the acylphosphate moieties relative to the oxazolone moieties.

Solvent and temperature conditions for forming the thiohydantoin product are generally the same as those discussed above for carboxyl activation, except that use of dimethylformamide is less preferable.

Figure 4:
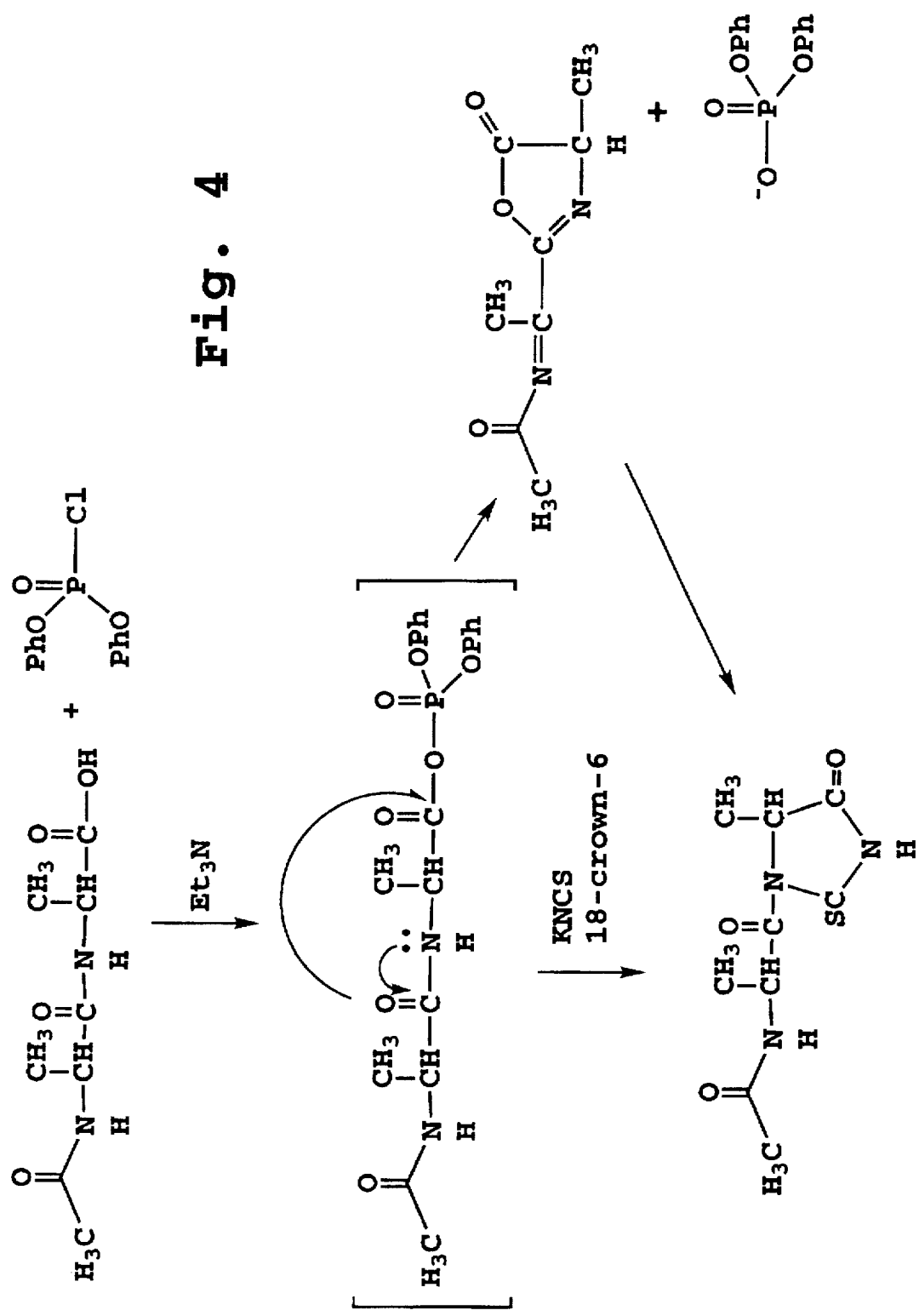
FIG. 4 shows a reaction scheme of the present invention in which diphenylchlorophosphate is reacted with acetylalanylalanine to give an acylphosphate intermediate which eliminates diphenyl phosphate to form an oxazolone which is further reacted with potassium thiocyanate in the presence of 18-crown-6 or $NH_4SCN$ to form an acetylalanylalanine thiohydantoin.

FIG. 4 illustrates a reaction scheme for preparing an exemplary N-protected amino acid thiohydantoin (Example 1). N-acetyl-Ala-Ala dipeptide was dissolved in acetonitrile and reacted with one equivalent of tetraphenylpyrophosphate (TPPP) in the presence of one equivalent of diisopropylethylamine (DIEA). After the mixture was heated at 60° C. for 5 minutes, the oxazolone product was reacted with ammonium thiocyanate in the presence of trifluoroacetic acid (TFA) Heating of the reaction mixture at 60° C. for 10 minutes afforded N-acetyl-Ala-Ala thiohydantoin product in 100% yield.

The procedures described above can also be used for forming free amino acid thiohydantoins for use, for example, as TH standards for HPLC identification of amino acid THs.

III. Application of the Method to C-Terminal Sequencing

Another application of the method of the invention is for use in a C-terminal amino acid sequencing procedure. In this method, the N-protected amino acid which is to be converted to the amino acid TH is the C-terminal amino acid residue of an N-protected peptide. The sequencing procedure can be adapted for automated or semi-automated operation, as will be described below.

A C-terminal sequencing method, in accordance with one aspect of the invention, is illustrated in FIGS. 5A–5E. The solid support can be prepared with any surface functional group which can bind the polypeptide, including functional groups placed on the surface by chemical derivatization. For instance, the solid support can be a particle bead having surface amine groups that are suitably derivatized to serve as a site of attachment, e.g., with a bifunctional crosslinking reagent such as disuccinimidyl suberate, although any of a variety of methods for coupling a peptide to a solid support can be employed. Examples of immobilization of peptides on resin and glass beads are presented in U.S. Pat. No. 5,185,266, which disclosure is incorporated herein by reference, and are suitable for practice of the present invention. Alternatively, the solid support can be a membrane which has been suitably derivatized to bind polypeptides. A preferred solid support which can be derivatized is a poly (vinylidene difluoride) membrane derivatized with carboxylic acid groups (PVDF-COOH), which can be obtained from Pall Corporation (Long Island, N.Y.).

Figure 5A:
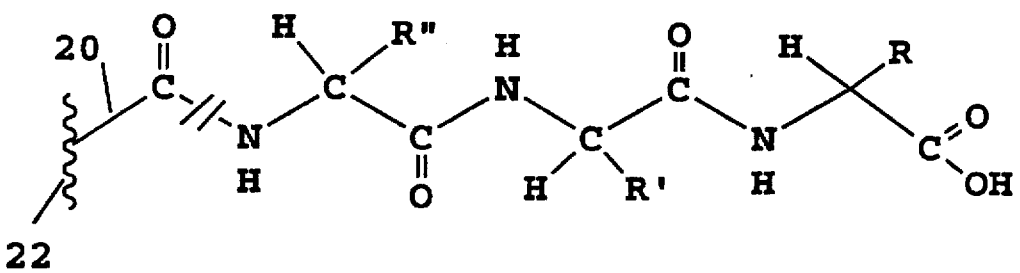
Figure 5B:
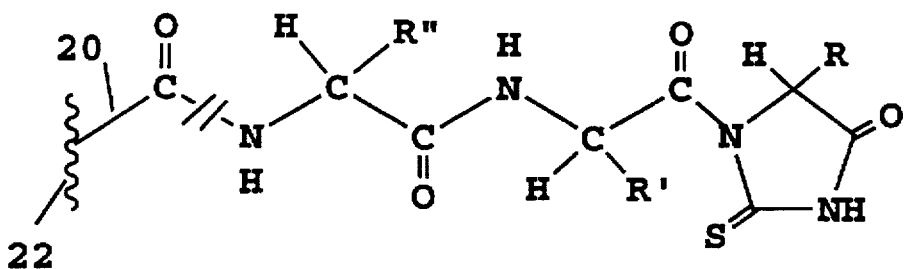

In the first step of the method, the immobilized peptide illustrated in FIG. 5A is reacted with a carboxyl-activating compound in the presence of base to form an acylphosphate which in the case of the terminal carboxyl immediately cyclizes to an oxazolone with release of di-substituted phosphate, as discussed in the preceding section. The oxazolone is then reacted with a thiocyanate reagent, as described above, to produce a thiohydantoin, i.e., a peptidyl thiohydantoin, as illustrated in FIG. 5B. The thiohydantoin is then cleaved from the next-in residue, e.g., by hydrolytic cleavage of the terminal amide bond, under acidic or basic conditions.

Figure 5C:
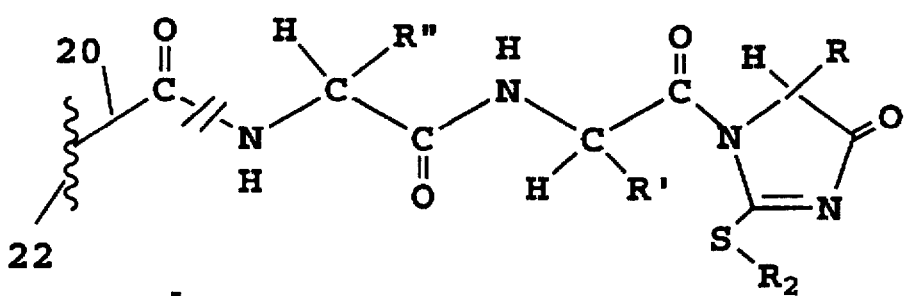

Alternatively, this cleavage can be facilitated by first alkylating the thiohydantoin, under basic conditions, to form an alkylated TH product, as illustrated in FIG. 5C. Preferred alkylating reagents and conditions are described in U.S. Pat. No. 5,185,266, the disclosure of which is incorporated herein by reference.

When an alkylating reagent is employed, the cleavage reaction can be performed directly under acidic anhydrous conditions with a thiocyanate anion, as depicted in FIG. 5D. Cleavage in the presence of a thiocyanate reagent, such as TMS-ITC or $NH_4SCN$, is preferred since reaction with the thiocyanate reagent under anhydrous acidic conditions is effective to form a new TH at the next-in C-terminal amino acid residue, as illustrated in FIG. 5E. This reaction may proceed through the activated peptidyl NCS intermediate shown in FIG. 5D. A metallothiocyanate/crown ether complex under acidic conditions can be used to cleave the alkylated thiohydantoin, with simultaneous formation of the next-in peptidyl thiohydantoin.

In some cases, it may be preferable to cleave the TH from the C-terminal end of the peptide by direct hydrolysis under acidic or basic conditions, to form a C-terminal residue with a free carboxyl group. This residue can then be converted efficiently to the corresponding TH by reaction with a reactive phosphate compound, and a thiocyanate reagent, as above.

In another aspect, the invention relates to improvements in the sequencing of serine, threonine, aspartate, and glutamate residues.

Figure 6:
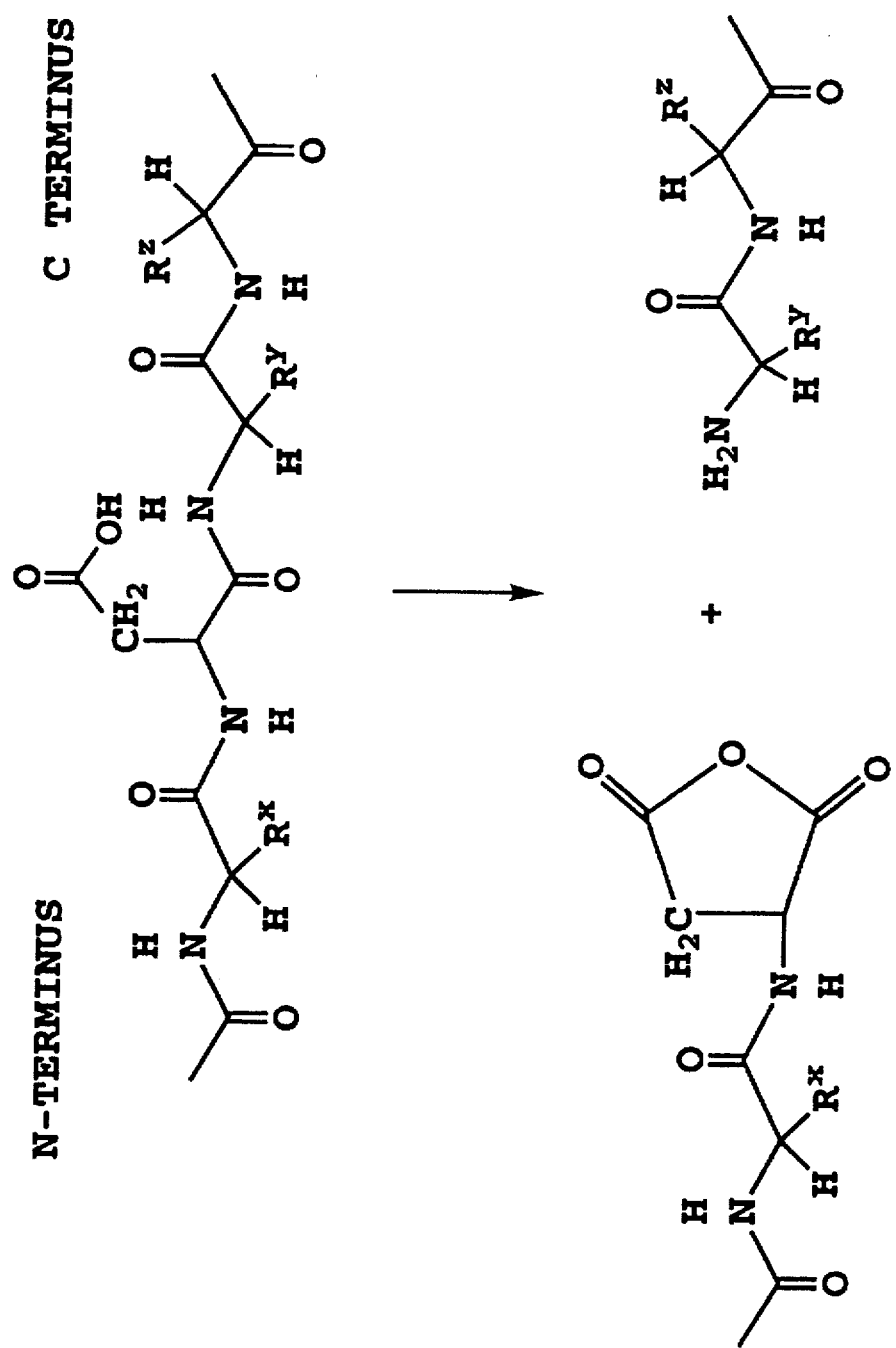
FIG. 6 shows cleavage of a polypeptide chain caused by reaction of the $\beta$-carboxylic acid group of an aspartate residue with the polypeptide backbone.

Studies carried out in support of the invention indicate that internal aspartate residues can mediate internal cleavage of the polypeptide backbone in the peptide being sequenced. A mechanism for such cleavage is illustrated in FIG. 6.

In the mechanism, a carboxyl oxygen in an aspartate residue reacts with the carbonyl carbon in the amide linkage on the. C-terminal side of the aspartate residue, thereby severing the polypeptide backbone at that point and forming a cyclic anhydride. In the next cycle of sequencing, the cyclic anhydride can react with thiocyanate reagent to form a new C-terminal thiohydantoin which is cosequenced along with TH derivatives from the true C-terminus of the polypeptide. The presence of multiple aspartate residues in a polypeptide can be particularly problematic, since internal cleavage of the peptide backbone will lead to the formation of multiple amino acid thiohydantoins in each sequencing step.

It has also been found that the thiohydantoins of aspartate and glutamate residues are typically not detectable, or are detectable only in small amounts, with the side chain carboxylates in unmodified form.

According to one aspect of the invention, the applicants have discovered that the above-mentioned difficulties with aspartate and glutamate residues can be diminished substantially by esterification of the carboxylate side chains in these residues. Such esterification can be conveniently carried out after phosphorylation of the peptide, as discussed below.

Esterification of an N-protected polypeptide may be conveniently carried out in an automated sequencer by use of a wash step in which the peptide is bathed in a selected alcohol as solvent (e.g., methanol, ethanol). Preferably, the esterification conditions include an acid (e.g., TFA) to facilitate esterification. For example, after the solid support has been wetted or immersed with a selected alcohol, the support can be exposed to the vapors of anhydrous trifluoroacetic acid to acidify the support.

When hydrocinnamic acid acyl-phosphate, prepared as above, was heated in acetonitrile with one equivalent of TMS-NCS for 10 minutes at 60° C., no reaction occurred, as judged by $^1$H-NMR analysis. Subsequent addition of naphthalenemethanol and TEA (one equivalent each) to the mixture, with heating, afforded the hydrocinnamate naphthylmethyl ester as above. These results indicate that the phosphorylated side chain carboxylates of aspartate and glutamate are not degraded when exposed to thiocyanate reagent.

Other studies conducted in support of the invention indicate that esterification of internal aspartate residues can suppress or eliminate internal cleavage at aspartate residues, so that only TH derivatives from the true C-terminus of the original peptide are observed during sequencing.

According to another aspect of the invention, the applicants have discovered that the above-mentioned difficulties with aspartate and glutamate residues can be diminished substantially by amidation of the carboxylate side chains in these residues. Such amidation can be conveniently carried out during acylphosphate formation.

Amidation of acylphosphate moieties of an N-protected polypeptide may be conveniently carried out in an automated sequencer by use of a wash step in which the peptide is bathed in a selected nucleophilic amine. Preferably, the amidation conditions include a base to facilitate amidation.

Serine and threonine residues can also be problematic to C-terminal sequencing, presumably because of interference by the side chain hydroxyl groups of these residues. For example, studies using the sequencing method disclosed in U.S. Pat. No. 5,185,266 (illustrated in FIGS. 5A-5E herein) have shown that when activation of the C-terminal carboxylate in a serine- or threonine-containing peptide is carried out with Woodward's Reagent K, sequencing halts at the sequencing cycle for the residue which immediately precedes a serine or threonine residue in the peptide. Accordingly, it would be desirable to chemically modify the side chain hydroxyl groups so that such problems are reduced.

Figure 7A:
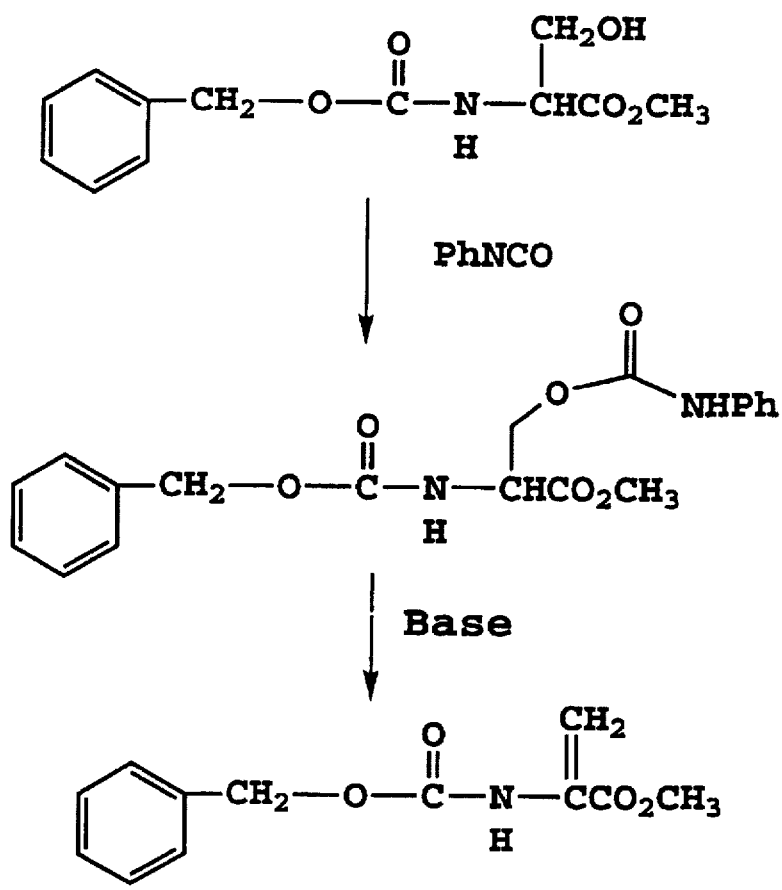
FIG. 7A shows reaction of N-carbobenzoxy-serine methyl ester with phenylisocyanate (PhNCO) followed by base treatment to give a dehydrated serine analog.
Figure 7B:
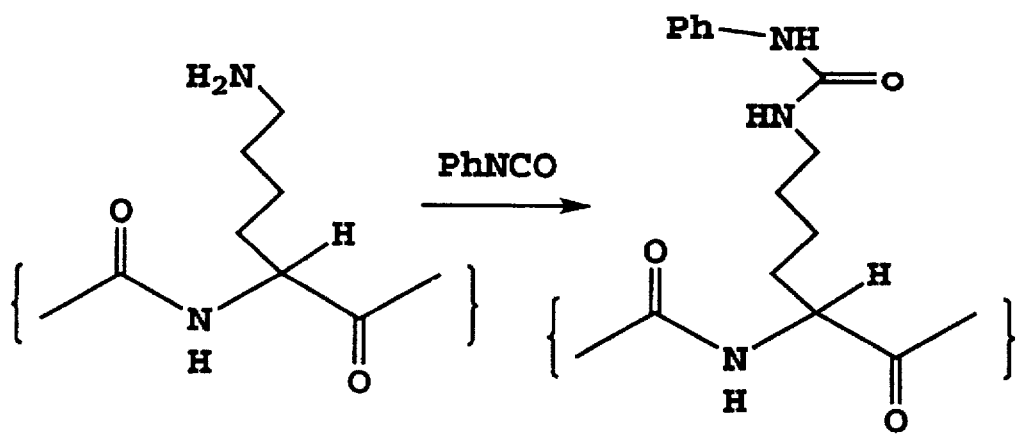
FIG. 7B shows reaction of phenylisocyanate with the $\epsilon$-amino group of a lysine residue.
Figure 8A:
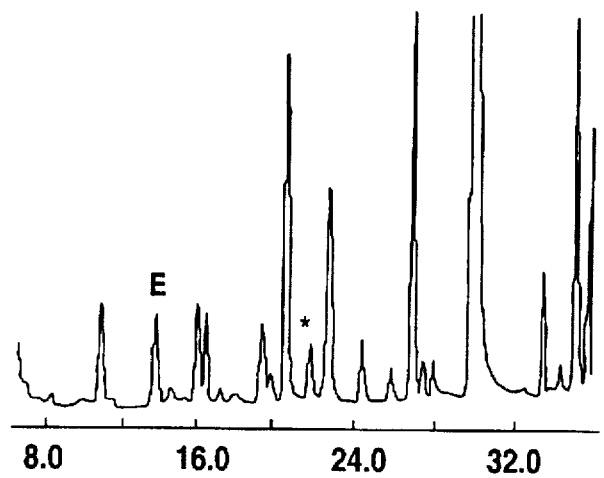
FIGS. 8A–8F shows HPLC chromatograms for the first to sixth reaction cycles in the C-terminal sequence analysis of cytochrome C, which was reacted with phenylisocyanate prior to thiohydantoin formation.
Figure 8B:
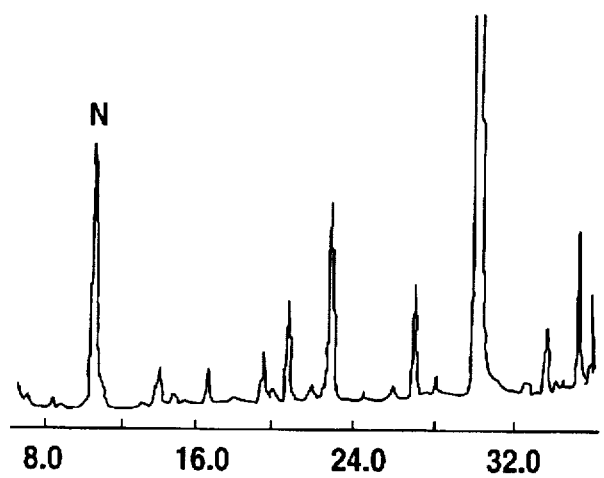
Figure 8C:
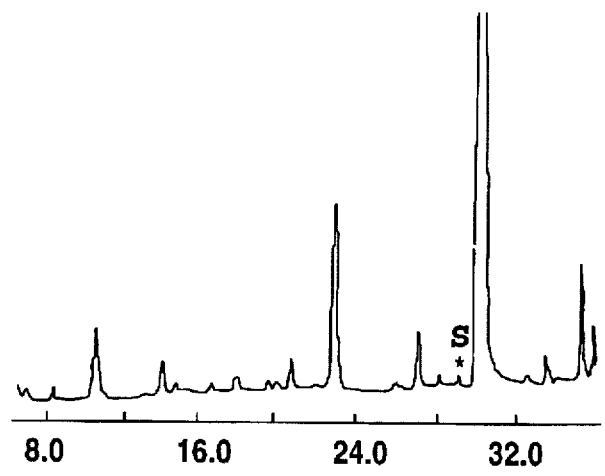
Figure 8D:
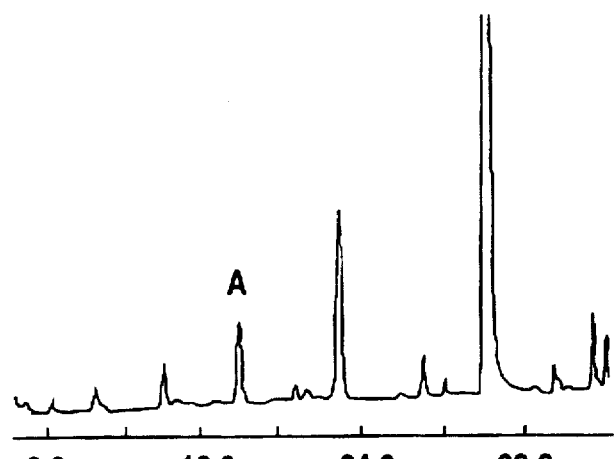
Figure 8E:
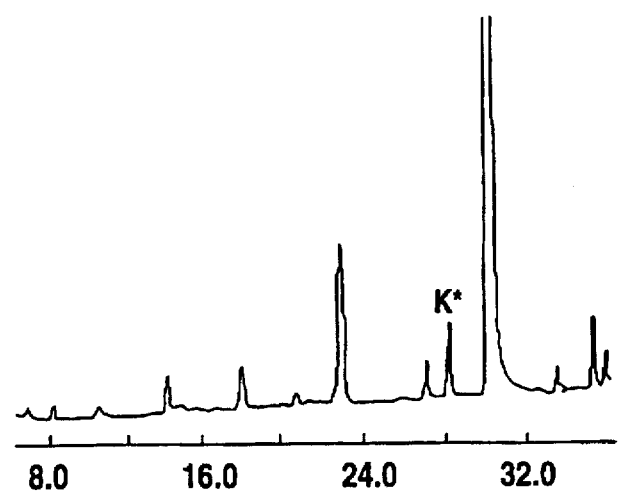
Figure 8F:
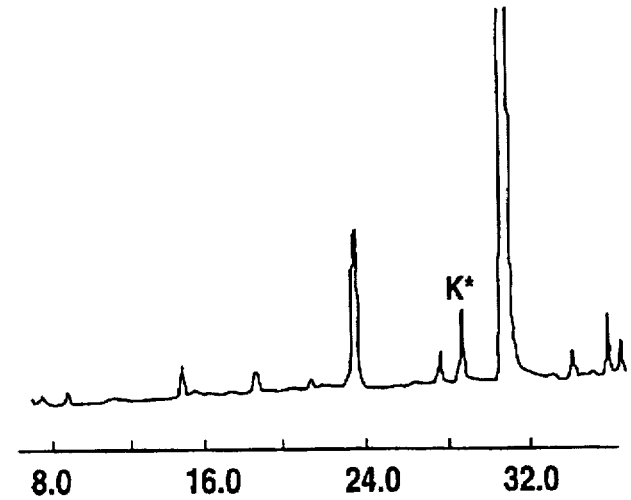
Figure 9A:
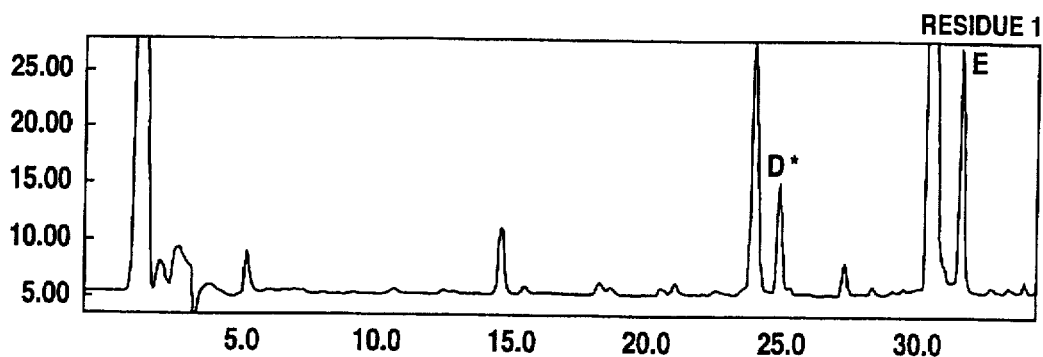
FIGS. 9A–9D show chromatograms of the released alkylated thiohydantoins from the first four sequencing cycles of a protein sample (RecA) having a glutamic acid residue in position 2 relative to the C-terminus and an aspartic acid residue in position 3 relative to the C-terminus.
Figure 9B:
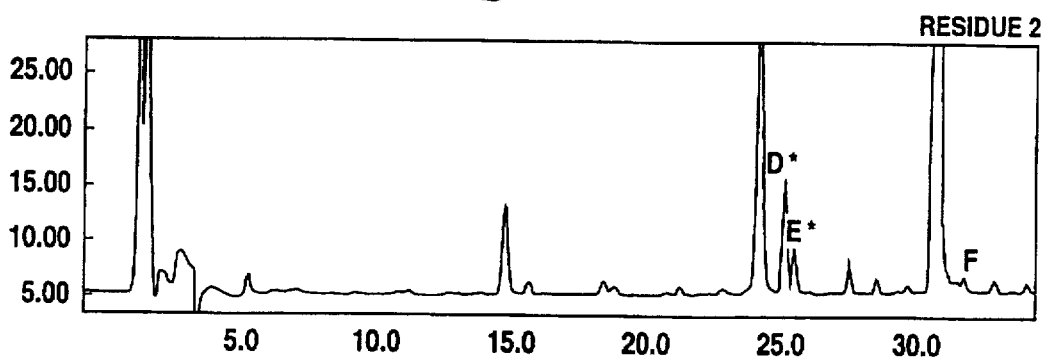
Figure 9C:
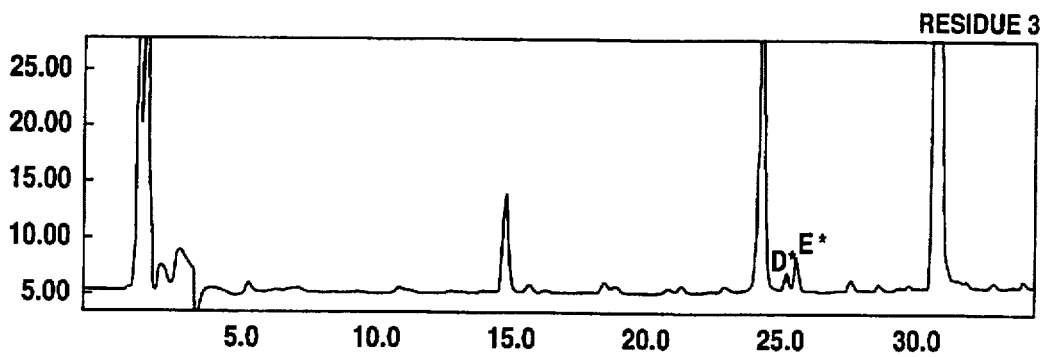
Figure 9D:
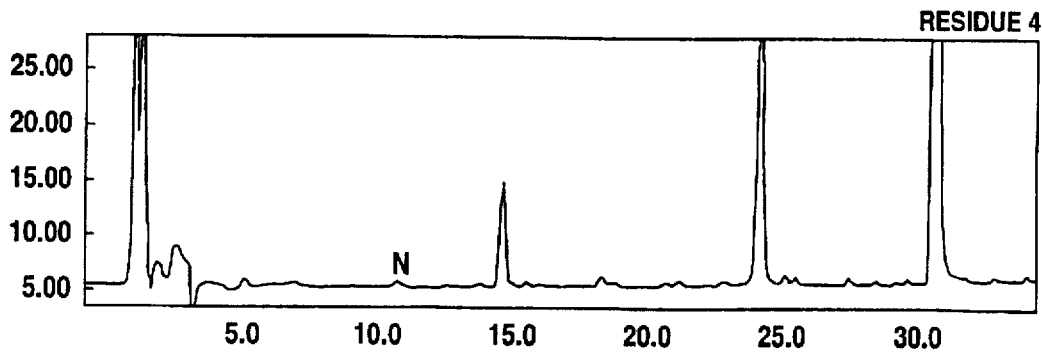
Figure 10A:
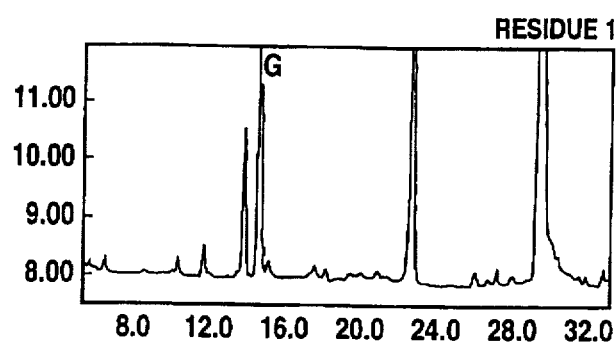
FIGS. 10A–10J show chromatograms of the released alkylated thiohydantoins from the first ten sequencing cycles of a protein sample (horse apomyoglobin).
Figure 10B:
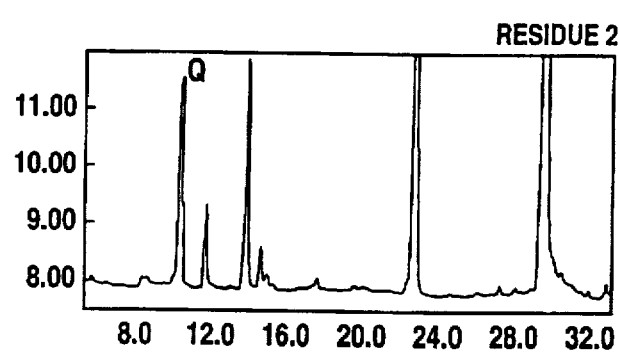
Figure 10C:
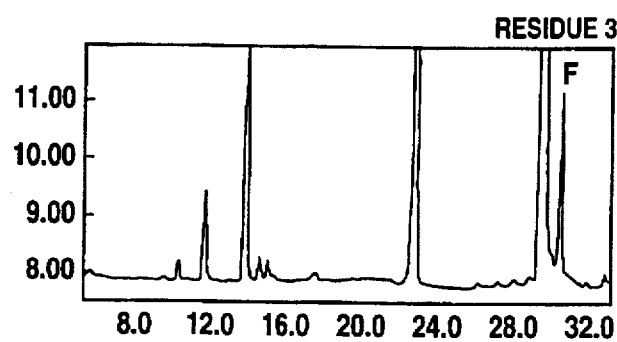
Figure 10D:
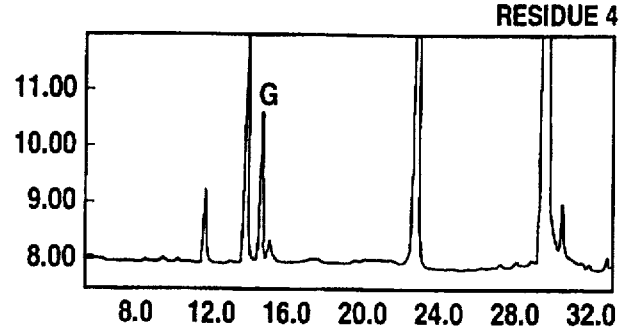
Figure 10E:
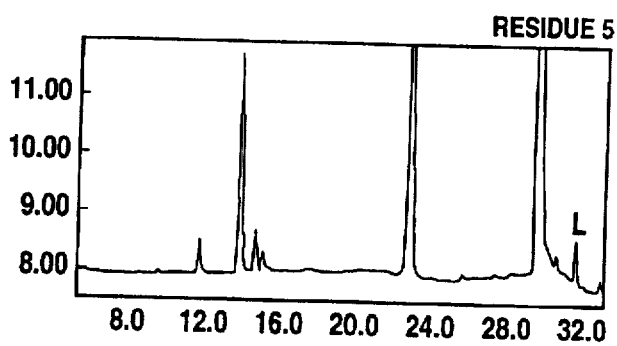
Figure 10F:
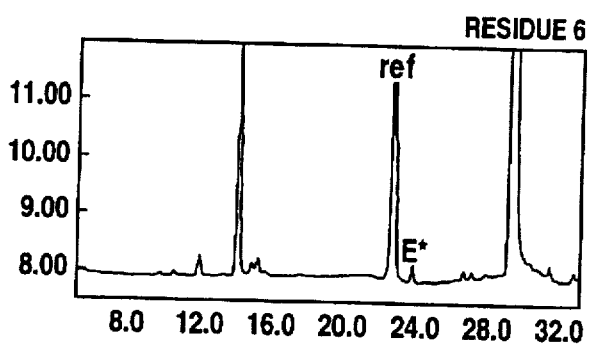
Figure 10G:
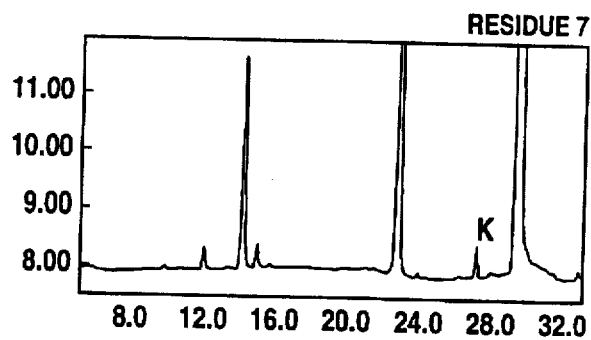
Figure 10H:
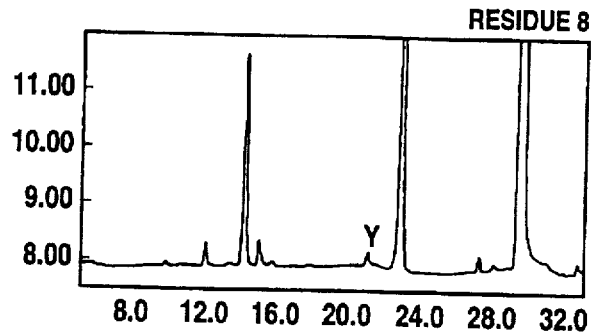
Figure 10I:
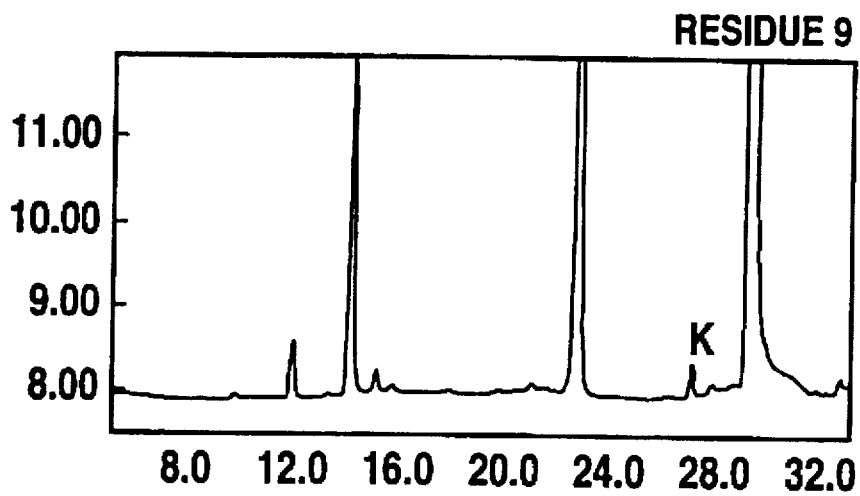
Figure 10J:
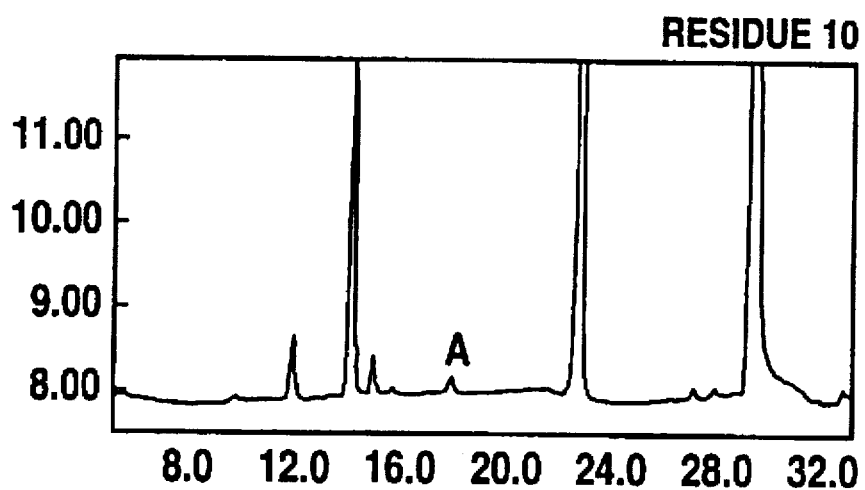

Dehydration of serine and threonine residues may be effected by treatment of peptides with phenylisocyanate (PhNCO). As illustrated in FIG. 7A, PhNCO can react with the hydroxyl group of a serine or threonine residue to produce a urethane derivative. Treatment of the urethane derivative with base leads to elimination of PhNCO$_2$H (PhNH$_2$ and CO$_2$), resulting in formation of the dehydrated analog of serine or threonine. A further advantage of phenylisocyanate treatment is that the ε-amino groups of lysine residues are converted to phenylurea groups (FIG. 7B). This derivatization reaction thus enhances detection of lysine as a single modified derivative.

Reaction of a polypeptide with phenylisocyanate is conducted prior to activation of the C-terminal carboxyl group of the polypeptide. Typically, the polypeptide is first immobilized on a solid support as described above, prior to reaction with phenylisocyanate. The immobilized polypeptide is then contacted with a solution of PhNCO (e.g., 0.2M) in acetonitrile for a time (e.g., 1–60 minutes) sufficient to derivatize all of the lysine, serine, and threonine residues in the peptide with phenylisocyanate. After the reaction is complete, the immobilized polypeptide is contacted with a solution containing base (e.g., 0.05–1.0M triethylamine or pyridine in acetonitrile) for a time sufficient to catalyze the elimination of PhNCO$_2$H from any serine and threonine residues that are present in the peptide. The immobilized peptide may then be sequenced by methods described above.

The utility of treatment with phenylisocyanate is illustrated in FIGS. 8A-8F. In this study, cytochrome C which had been immobilized on an activated PVDF membrane (Example 2) was treated with phenylisocyanate and base as just described, to convert the internal threonine residue at C-terminal position 3 to a dehydrated analog of threonine, and to convert the lysine residues at positions 5 and 6 to the corresponding urea derivatives. The polypeptide was then treated with POCl(OPh)$_2$ in the presence of TEA as described above, and then with ammonium thiocyanate to form the C-terminal thiohydantoin derivative. C-Terminal sequencing of the peptide was then conducted using the method shown in FIG. 5A-5E. The HPLC chromatograms from the first six sequencing cycles are shown in FIGS. 8A-8F.

As can be seen, the method was successful in identifying correctly five of the first six C-terminal residues in the peptide. The sole exception was the threonine residue in cycle 3, for which no TH derivative could be detected. In addition, each lysine residue at position 5 and 6 in the sequence was detected as a large thiohydantoin peak which corresponded to the ε-nitirogen phenylurea derivative. These results illustrate how prior treatment of a polypeptide with phenylisocyanate can (1) provide sequencing of at least three residues following a threonine residue, and (2) enhance the detection of lysine residues by conversion to a single, stable derivative which is compatible with C-terminal sequencing.

It is possible using the method of the invention to routinely activate a protein or peptide on an automated sequencer, for example, an Applied Biosystems Sequencer Model 477 A in five to thirty minutes at room temperature, although the reaction can also be carried out efficiently at, for example, 55° C., consistent with the reaction temperature of subsequent steps. On-line activation with an activated phosphate compound of the invention can help to minimize time-consuming sample preparation steps prior to sequencing.

The above-detailed sequencing technique is readily automated using equipment ordinarily employed for the automated N-terminal sequencing of peptides. One embodiment of a device for automatically sequencing a peptide from the C-terminal end employs a surface-immobilized peptide contained in a reaction vessel to which fresh solvent and reagents are added, and from which reaction mixtures and solvent washes are removed. The released amino acid thiohydantoin is extracted from the support and transferred to an on-line HPLC for analysis.

The following examples illustrate, but in no way are intended to limit the present invention.

EXAMPLE 1

Synthesis of Ac-Ala-Ala-TH Using Diphenylchlorophosphate

Acetyl-alanine-alanine (Ac-Ala-Ala-OH) (75 mg, Bachem, Philadelphia, Pa.) was dissolved in $CH_3CN$ (1 mL) and reacted with one equivalent each of triethylamine (TEA, 51 uL) and diphenylchlorophosphate ($POCl(OPh)_2$, 76 uL). After the reaction had been allowed to proceed for 10 minutes, precipitated TEA·HCl was removed by filtration.

After removal of the precipitate, a premixed solution containing one equivalent each of potassium thiocyanate and 18-crown-6 was added to the acylphosphate solution, followed by 1 drop of trifluoroacetic acid (TFA). Yield of the Ac-Ala-Ala-TH product, as judged by $^1H$-NMR, was 50%. The same procedure, except using $NH_4SCN$ in place of potassium thiocyanate and 18-crown-6, led to 100% yield of product.

EXAMPLE 2

Formation of Immobilized Peptidyl-Thiohydantoins on Activated Membrane Support For the following procedures, a carboxylate-derivatized polyvinylidene difluoride membrane was used (PVDF-COOH membrane, obtained from Pall Corporation, Long Island, N.Y.).

A. Conversion of Membrane Carboxylate Groups to Activated Enol Esters

A solution of a reactive ketenimine was generated in acetonitrile ($CH_3CN$) from N-ethyl-5-phenylisoxazolium sulfonate (Woodward's Reagent K, WRK) by mixing 0.063 g WRK (0.025 mole) and 0.5 mL diisopropylethylamine (DIEA, 0.025 mole) in 2 mL $CH_3CN$. This solution was used immediately upon complete dissolution of the solid WRK. The carboxyl-derivatized (PVDF-COOH) membrane was bathed in this solution (scaled-up as necessary to completelyimmerse the support) for 4–6 hours. The resultant enol ester ("activated") membrane support was then washed several times with $CH_3CN$, and finally with acetone and allowed to air-dry briefly. The dried, activated membrane support was then kept in a capped Eppendorf or a sealed plastic bag (no special drying atmosphere was employed).

B. Attachment of Polypetides to Activated Membrane Support

B. 1 Attachment of Large Proteins

Typically, a protein dissolved in a buffered aqueous solution (pH 1 to 8) is shaken the activated membrane support for between 3 hours and overnight at room temperature. At pH 7, a 0.1M phosphate buffer is typically used, at pH 1 a 0.1% TFA solution is typically employed.

120 moles of protein (e.g., cytochrome C) was dissolved in 3 ml of pH 7 phosphate buffer (100 mM). This solution was sloshed around over a 286 mg sheet of activated PVDF membrane for 3 hours. Amino acid analysis was used to determine that 150 μmole/mg of protein was attached. The attachment yield was 36%.

B.2 Attachment of Short Peptides

Typically, a small peptide (~15 amino acid residues) dissolved in an organic solvent, such as N-methyl pyrrolidone (NMP), was shaken over the activated membrane support (section A) for between 3 hours and overnight at room temperature.

2 mg of a 13-residue peptide K13E was dissolved in 3 ml NMP. This solution was sloshed around over a 286 mg sheet of the activated PVDF for 3 hours (the activated PVDF sheet had been prepared 2 days previously). Unbound peptide was washed away and the sheet placed in a sequencer to determine the peptide sequence.

C. Formation of Immobilized Peptidyl-Thiohydantoin in an Automated Sequencer

Proteins and peptides attached to the membrane support as described in section B were converted to C-terminal thiohydantoins and then sequenced from the C-terminus using an Applied Biosystems Model 477A Protein Sequencer. A 10% solution of DIEA in acetonitrile was loaded in the S1 position of the Model 477A, and an 8% solution of diphenylchlorophosphate in acetonitrile was placed in the X1 position.

The following reaction steps were carried out at 55° C. After the protein- or peptide-derivatized membrane support had been loaded in the sequencer, equi-volume aliquots of the DIEA and diphenylchlorophosphate solutions were delivered to the membrane in an amount sufficient to completely wet the membrane. After a 5 minute pause, delivery of the DIEA and diphenylchlorophosphate solutions to the membrane was repeated once. The membrane was then washed with acetonitrile to remove residual chlorophosphate compound. After another 5 minute pause, an aliquot of 1% ammonium thiocyanate in acetonitrile was delivered to thee membrane, followed by exposure of the membrane to trifluoroacetic acid (TFA) vapor for 60 seconds. After a 5 minute pause, delivery of 1% ammonium isothiocyanate and TFA vapor was repeated 1–5 additional times, with intervening 5 minute pauses. Residual reagents were then washed from the membrane using acetonitrile.

If esterification of the carboxylate groups of aspartate and glutamate side chains was desired, an esterification step was included after formation of peptidyl-thiohydantoin and washing of the membrane with acetonitrile as above. In the esterification step, the membrane was washed briefly (e.g., 1 minute) with methanol, followed by treatment with TFA vapor for 60 seconds. After a 5 minute pause, the membrane was washed with acetonitrile.

Sequencing was performed essentially as described in U.S. Pat. No. 5,185,266. In this procedure, the C-terminal thiohydantoin is reacted with an alkylating reagent to make the thiohydantoin a better leaving group (FIGS. 5A–5E herein). TMS-ITC or ammonium thiocyanate and TFA vapor are then used to cleave the thiohydantoin adduct from the remaining peptide to form a thiohydantoin of the next-in amino acid residue.

Cleaved thiohydantoin adducts were isolated and identified by the methods presented in U.S. Pat. No. 5,185,266, which are suitable for practice of the present invention.

EXAMPLE 3

C-Terminal Sequencing of a Test Proteins using Tetraphenylpyrophosphate and either ammonium thiocyanate or piperidine thiocyanate 500 pmol samples consisting of either RecA protein or horse apomyoglobin were non-covalently attached to separate ProSpin (a non-functionalized polyvinylidene difluoride membrane) sample cartridges (Applied Biosystems, Foster City, Calif.) using manufacturer's protocols and then sequenced from the C-terminus using an Applied Biosystems Model 477A Protein Sequencer. The sequencing protocol followed was essentially the same as that described in Boyd et al, Anal. Biochemistry, 206:344–352 (1992) and Boyd et al, U.S. Pat. No. 5,185,266, except for the modifications indicated below. For RecA protein, the start-up cycle consisted of the steps listed in Table II, which is appropriate for proteins having aspartic acid and/or glutamic acid residues within their C-terminal regions. For horse apomyoglobin and subsequently for RecA, cycles consisted of the steps listed in Table III. Reagents were assigned to the bottle locations of the 477A sequencer in accordance with the following table:

TABLE I

C-terminal reagent configuration for Model 477A Protein Sequencer

| Bottle Position | Reagent | Use |
|---|---|---|
| R1 | NH₄NCS | Amidation Cleavage |
| R2 | TFA (vapor) | Activation Cleavage |
| R3 | 2-bromomethylnaphthalene | Alkylation of TH |
| R4 | acetonitrile | Wash |
| R5 | TFA (liquid) | Standard deprotection |
| X1 | tetraphenylpyrophosphate (TPPP) | Carboxyl-activation |
| X2 | Boc-protected alkylated TH standards | Standard |
| S1 | 10% DIEA | Activation Alkylation |
| S2 | piperidine thiocyanate | Amidation TH cleavage |
| S3 | acetonitrile | Transfer solvent |
| S4 | 20% acetonitrile | alkylated TH reconstitution |

The following reaction steps were carried out at 55° C. After the sample was loaded in the sequencer, equi-volume aliquots of the DIEA and TPPP solutions were delivered to the ProSpin membrane in an amount sufficient to completely wet the membrane. After a 100 sec pause, an aliquot of 3% ammonium thiocyanate in acetonitrile was delivered to the membrane, followed by exposure to trifluoroacetic acid (TFA) vapor for up to 60 sec, followed by a minute pause. This sequence of steps was repeated 1–5 additional times, with the membrane being washed with acetonitrile between each such cycle. If amidation of the carboxylate groups of aspartate and/or glutamate side chains was desired, an amidation step was included after formation of the peptidyl-oxazolone with TPPP and DIEA, but before delivery of NH₄SCN/TFA. In the amidation step, piperidine-HSCN is delivered after the 100 sec pause following the delivery of TPPP and DIEA. Conditions are left basic, i.e. no TFA delivery. After a 5 min pause, the membrane was washed with acetonitrile. These steps are repeated two additional times. In order to make the thiohydantoin from the oxazolone at the C-terminus, the series of step described above is followed.

Finally, at each sequencing cycle, the C-terminal thiohydantoin was reacted with an alkylating agent as taught in U.S. Pat. No. 5,185,266. Ammonium thiocyanate and TFA vapor are the used to cleave the thiohydantoin adduct form the remaining protein. The cleaved thiohydantoin adducts were isolated and detected as taught in U.S. Pat. No. 5,185,266.

Results of shown in the chromatograms of FIGS. 9A–9D (RecA) and 10A–10J (horse apomyoglobin).

TABLE II

Model 477A Start-up Cycle Steps for Asp- and/or Glu-Containing Protein or Peptide Samples
(Total cycle time: 72 min 59 sec)

| Step | Function | Elapsed Time |
|---|---|---|
| 1 | Deliver S3 | 3 min 20 sec |
| 2 | Argon Dry | 6 min 40 sec |
| 3 | Prep S1 | 7 min 0 sec |
| 4 | Deliver S1 | 7 min 6 sec |
| 5 | Argon Dry | 7 min 14 sec |
| 6 | Prep X1 | 7 min 20 sec |
| 7 | Deliver X1 | 7 min 23 sec |
| 8 | Argon Dry | 7 min 31 sec |
| 9 | Pause | 9 min 11 sec |
| 10 | Prep S2 | 9 min 31 sec |
| 11 | Delivery S2 | 9 min 37 sec |
| 12 | Argon Dry | 9 min 46 sec |
| 13 | Pause | 14 min 46 sec |
| 14 | Prep S3 | 15 min 6 sec |
| 15 | Deliver S3 | 15 min 26 sec |
| 16 | Argon Dry | 15 min 46 sec |
| 17 | Deliver S3 | 16 min 6 sec |
| 18 | Pause | 16 min 26 sec |
| 19 | Argon Dry | 16 min 46 sec |
| 20 | Prep S1 | 17 min 6 sec |
| 21 | Deliver S1 | 17 min 12 sec |
| 22 | Argon Dry | 17 min 20 sec |
| 23 | Prep X1 | 17 min 26 sec |
| 24 | Deliver X1 | 17 min 29 sec |
| 25 | Argon Dry | 17 min 37 sec |
| 26 | Pause | 19 min 17 sec |
| 27 | Prep S2 | 19 min 37 sec |
| 28 | Deliver S2 | 19 min 43 sec |
| 29 | Argon Dry | 19 min 52 sec |
| 30 | Pause | 24 min 52 sec |
| 31 | Prep S3 | 25 min 12 sec |
| 32 | Deliver S3 | 25 min 32 sec |
| 33 | Pause | 25 min 52 sec |
| 34 | Argon Dry | 26 min 12 sec |
| 35 | Deliver S3 | 26 min 32 sec |
| 36 | Pause | 26 min 52 sec |
| 37 | Argon Dry | 27 min 12 sec |
| 38 | Prep S1 | 27 min 32 sec |
| 39 | Deliver S1 | 27 min 38 sec |
| 40 | Argon Dry | 27 min 46 sec |
| 41 | Prep X1 | 27 min 52 sec |
| 42 | Deliver X1 | 27 min 55 sec |
| 43 | Argon Dry | 28 min 3 sec |
| 44 | Pause | 29 min 43 sec |
| 45 | Prep S2 | 30 min 3 sec |
| 46 | Deliver S2 | 30 min 9 sec |

TABLE II-continued

Model 477A Start-up Cycle Steps for Asp- and/or Glu-Containing Protein or Peptide Samples
(Total cycle time: 72 min 59 sec)

| Step | Function | Elapsed Time |
|---|---|---|
| 47 | Argon Dry | 30 min 17 sec |
| 48 | Pause | 35 min 17 sec |
| 49 | Prep S3 | 35 min 37 sec |
| 50 | Deliver S3 | 35 min 57 sec |
| 51 | Pause | 36 min 17 sec |
| 52 | Argon Dry | 36 min 37 sec |
| 53 | Deliver S3 | 36 min 57 sec |
| 54 | Pause | 37 min 17 sec |
| 55 | Argon Dry | 37 min 37 sec |
| 56 | Prep S1 | 37 min 57 sec |
| 57 | Deliver S1 | 38 min 3 sec |
| 58 | Argon Dry | 38 min 11 sec |
| 59 | Prep X1 | 38 min 17 sec |
| 60 | Deliver X1 | 38 min 20 sec |
| 61 | Argon Dry | 38 min 28 sec |
| 62 | Pause | 40 min 8 sec |
| 63 | Prep R1 | 40 min 14 sec |
| 64 | Deliver R1 | 40 min 17 sec |
| 65 | Argon Dry | 40 min 25 sec |
| 66 | Prep R2 | 40 min 31 sec |
| 67 | Deliver R2 | 40 min 51 sec |
| 68 | Load S3 | 41 min 11 sec |
| 69 | Block Flush | 41 min 31 sec |
| 70 | Pause | 46 min 31 sec |
| 71 | Deliver S3 | 47 min 31 sec |
| 72 | Argon Dry | 47 min 51 sec |
| 73 | Prep S1 | 48 min 11 sec |
| 74 | Deliver S1 | 48 min 17 sec |
| 75 | Argon Dry | 48 min 25 sec |
| 76 | Prep X1 | 48 min 31 sec |
| 77 | Deliver X1 | 48 min 34 sec |
| 78 | Argon Dry | 48 min 42 sec |
| 79 | Pause | 50 min 22 sec |
| 80 | Prep R1 | 50 min 28 sec |
| 81 | Deliver R1 | 50 min 31 sec |
| 82 | Argon Dry | 50 min 39 sec |
| 83 | Prep R2 | 50 min 45 sec |
| 84 | Deliver R2 | 51 min 5 sec |
| 85 | Load S3 | 51 min 25 sec |
| 86 | Block Flush | 51 min 45 sec |
| 87 | Pause | 56 min 45 sec |
| 88 | Deliver S3 | 57 min 15 sec |
| 89 | Argon Dry | 57 min 35 sec |
| 90 | Prep S1 | 57 min 55 sec |
| 91 | Deliver S1 | 58 min 1 sec |
| 92 | Argon Dry | 58 min 9 sec |
| 93 | Prep X1 | 58 min 15 sec |
| 94 | Deliver X1 | 58 min 18 sec |
| 95 | Argon Dry | 58 min 26 sec |
| 96 | Pause | 60 min 6 sec |
| 97 | Prep R1 | 60 min 12 sec |
| 98 | Deliver R1 | 60 min 15 sec |
| 99 | Argon Dry | 60 min 23 sec |
| 100 | Prep R2 | 60 min 29 sec |
| 101 | Deliver R2 | 60 min 49 sec |
| 102 | Load S3 | 61 min 9 sec |
| 103 | Block Flush | 61 min 29 sec |
| 104 | Pause | 66 min 29 sec |
| 105 | Deliver S3 | 66 min 59 sec |
| 106 | Pause | 67 min 19 sec |
| 107 | Deliver S3 | 67 min 49 sec |
| 108 | Pause | 68 min 9 sec |
| 109 | Argon Dry | 69 min 9 sec |
| 110 | Deliver S3 | 69 min 39 sec |
| 111 | Pause | 69 min 59 sec |
| 112 | Deliver S3 | 70 min 29 sec |
| 113 | Argon Dry | 71 min 29 sec |
| 114 | Deliver S3 | 71 min 59 sec |
| 115 | Argon Dry | 72 min 59 sec |

TABLE III

Model 477A Cycle Steps using TPPP and Ammonium Thiocyanate
(Total cycle time: 55 min 22 sec)

| Step | Function | Elapsed Time |
|---|---|---|
| 1 | Deliver S3 | 3 min 20 sec |
| 2 | Argon Dry | 6 min 40 sec |
| 3 | Prep S1 | 7 min 0 sec |
| 4 | Deliver S1 | 7 min 10 sec |
| 5 | Argon Dry | 7 min 18 sec |
| 6 | Prep X1 | 7 min 24 sec |
| 7 | Deliver X1 | 7 min 27 sec |
| 8 | Argon Dry | 7 min 35 sec |
| 9 | Pause | 9 min 15 sec |
| 10 | Prep R1 | 9 min 21 sec |
| 11 | Deliver R1 | 9 min 24 sec |
| 12 | Argon Dry | 9 min 32 sec |
| 13 | Load S3 | 9 min 52 sec |
| 14 | Block Flush | 10 min 12 sec |
| 15 | Prep R2 | 10 min 18 sec |
| 16 | Deliver R2 | 10 min 48 sec |
| 17 | Load S3 | 11 min 8 sec |
| 18 | Block Flush | 11 min 28 sec |
| 19 | Pause | 16 min 28 sec |
| 20 | Deliver S3 | 16 min 58 sec |
| 21 | Argon Dry | 17 min 18 sec |
| 22 | Prep S1 | 17 min 38 sec |
| 23 | Deliver S1 | 17 min 48 sec |
| 24 | Argon Dry | 17 min 56 sec |
| 25 | Prep X1 | 18 min 2 sec |
| 26 | Deliver X1 | 18 min 5 sec |
| 27 | Argon Dry | 18 min 13 sec |
| 28 | Pause | 19 min 53 sec |
| 29 | Prep R1 | 19 min 59 sec |
| 30 | Deliver R1 | 20 min 2 sec |
| 31 | Argon Dry | 20 min 10 sec |
| 32 | Load S3 | 20 min 30 sec |
| 33 | Block Flush | 20 min 50 sec |
| 34 | Prep R2 | 20 min 56 sec |
| 35 | Deliver R2 | 21 min 26 sec |
| 36 | Load S3 | 21 min 46 sec |
| 37 | Block Flush | 22 min 6 sec |
| 38 | Pause | 27 min 6 sec |
| 39 | Deliver S3 | 27 min 36 sec |
| 40 | Argon Dry | 27 min 56 sec |
| 41 | Prep S1 | 28 min 16 sec |
| 42 | Deliver S1 | 28 min 26 sec |
| 43 | Argon Dry | 28 min 34 sec |
| 44 | Prep X1 | 28 min 40 sec |
| 45 | Deliver X1 | 28 min 43 sec |
| 46 | Argon Dry | 28 min 51 sec |
| 47 | Pause | 30 min 31 sec |
| 48 | Prep R1 | 30 min 37 sec |
| 49 | Deliver R1 | 30 min 40 sec |
| 50 | Argon Dry | 30 min 48 sec |
| 51 | Load S3 | 31 min 8 sec |
| 52 | Block Flush | 31 min 28 sec |
| 53 | Prep R2 | 31 min 34 sec |
| 54 | Deliver R2 | 32 min 4 sec |
| 55 | Load S3 | 32 min 24 sec |
| 56 | Block Flush | 32 min 44 sec |
| 57 | Pause | 37 min 44 sec |
| 58 | Deliver S3 | 38 min 44 sec |
| 59 | Argon Dry | 39 min 4 sec |
| 60 | Prep S1 | 39 min 24 sec |
| 61 | Deliver S1 | 39 min 34 sec |
| 62 | Argon Dry | 39 min 42 sec |
| 63 | Prep X1 | 39 min 48 sec |
| 64 | Deliver X1 | 39 min 51 sec |
| 65 | Argon Dry | 39 min 59 sec |
| 66 | Pause | 41 min 39 sec |
| 67 | Prep R1 | 41 min 45 sec |
| 68 | Deliver R1 | 41 min 48 sec |
| 69 | Argon Dry | 41 min 56 sec |
| 70 | Load S3 | 42 min 16 sec |
| 71 | Block Flush | 42 min 36 sec |
| 72 | Prep R2 | 42 min 42 sec |
| 73 | Deliver R2 | 43 min 12 sec |
| 74 | Load S3 | 43 min 32 sec |

TABLE III-continued

Model 477A Cycle Steps using TPPP and Ammonium Thiocyanate
(Total cycle time: 55 min 22 sec)

| Step | Function | Elapsed Time |
|------|----------|--------------|
| 75 | Block Flush | 43 min 52 sec |
| 76 | Pause | 48 min 52 sec |
| 77 | Deliver S3 | 49 min 22 sec |
| 78 | Pause | 49 min 42 sec |
| 79 | Deliver S3 | 50 min 12 sec |
| 80 | Pause | 50 min 32 sec |
| 81 | Argon Dry | 51 min 32 sec |
| 82 | Deliver S3 | 52 min 2 sec |
| 83 | Pause | 52 min 22 sec |
| 84 | Deliver S3 | 52 min 52 sec |
| 85 | Argon Dry | 53 min 52 sec |
| 86 | Deliver S3 | 54 min 22 sec |
| 87 | Argon Dry | 55 min 22 sec |

While the invention has been described with reference to specific methods and embodiments, it will be appreciated that various modifications and changes may be made without departing from the invention.

It is claimed:

1. A method of converting an N-protected amino acid to a corresponding amino acid thiohydantoin, comprising reacting the N-protected amino acid, in the presence of a base, with a compound selected from the group consisting of $(R_1O)(R_2O)P(=O)X$ and $(R_1O)(R_2O)P(=O)-Y-P(=O)(OR_3)(OR_4)$ where $R_1$ and $R_2$ are each alkyl having up to 10 carbon atoms, aryl having up to 10 carbon atoms, or alkaryl having up to 8 carbon atoms, wherein $R_1$ and $R_2$ are the same or different and may be covalently linked to each other; X is bromine or chlorine; and Y is oxygen or sulfur; to form an activated, N-protected amino acid, and reacting the activated, N-protected amino acid with a thiocyanate reagent under conditions effective to convert the activated amino acid to an N-protected thiohydantoin.

2. The method of claim 1, wherein X is chlorine and Y is oxygen.

3. The method of claim 1, wherein the thiocyanate reagent is ammonium thiocyanate or piperidine thiocyanate.

4. The method of claim 1, wherein the N-protected amino acid is the C-terminal amino acid of a peptide or protein immobilized on a solid support.

5. The method of claim 4, for use in identifying the C-terminal amino acid residue of said peptide or protein, further comprising:

(a) placing the N-protected thiohydantoin under conditions effective to release an amino acid thiohydantoin from a residual peptide or protein; and (b) isolating and identifying the released amino acid thiohydantoin, thereby identifying the C-terminal residue of the peptide or protein.

6. The method of claim 1, wherein the compound selected is $(R_1O)(R_2)P(=O)-Y-P(=O)(OR_3)(OR_4)$.

7. The method of claim 6, wherein Y is oxygen.

8. The method of claim 6, wherein Y is sulfur.

9. The method of claim 4, wherein the compound selected is $(R_1O)(R_2O)P(=O)-Y-P(=O)(OR_3)(OR_4)$.

10. The method of claim 9, wherein Y is oxygen.

11. The method of claim 9, wherein Y is sulfur.

12. The method of claim 6, wherein $R_1$ through $R_4$ are phenyl.

13. The method of claim 6, wherein $R_1$ through $R_4$ are pyridyl.

14. The method of claim 6, wherein $R_1$ through $R_4$ are naphthyl.

15. The method of claim 6, wherein $R_1$ through $R_4$ are furyl.

16. The method of claim 1, wherein the compound selected is $(R_1O)(R_2O)P(=O)X$.

17. The method of claim 16, wherein X is Cl.

18. The method of claim 16, wherein $R_1$ and $R_2$ are phenyl.

19. The method of claim 16, wherein $R_1$ and $R_2$ are pyridyl.

20. The method of claim 16, wherein $R_1$ and $R_2$ are naphthyl.

21. The method of claim 16, wherein $R_1$ and $R_2$ are furyl.

22. The method of claim 5, wherein the N-protected amino acid thiohydantoin contains an aspartate or glutamate residue in the C-terminal region of the thiohydantoin, and wherein prior to step (a), the N-protected amino acid thiohydantoin is reacted with an alcohol to esterify the side chain carboxylate group of said residue.

23. The method of claim 5, wherein the N-protected amino acid thiohydantoin contains a serine or threonine residue in the C-terminal region, and wherein prior to step (a), the N-protected amino acid thiohydantoin is reacted with phenylisocyanate and a base under conditions effective to convert said residue to a dehydrated analog.

24. The method of claim 5, wherein the N-protected amino acid thiohydantoin contains a lysine residue in the C-terminal region, and wherein prior to step (a), the N-protected amino acid thiohydantoin is reacted with phenylisocyanate and a base under conditions effective to convert said residue to an ε-phenylurea analog.

* * * * *